United States Patent
Hetling et al.

(10) Patent No.: US 8,118,752 B2
(45) Date of Patent: Feb. 21, 2012

(54) APPARATUS AND METHODS FOR MAPPING RETINAL FUNCTION

(75) Inventors: John R. Hetling, Dyer, IN (US); Tamas Ban, Round Lake Beach, IL (US); Safa Rahmani, Northbrook, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 368 days.

(21) Appl. No.: 12/157,276

(22) Filed: Jun. 9, 2008

(65) Prior Publication Data

US 2008/0294066 A1    Nov. 27, 2008
US 2009/0281451 A2    Nov. 12, 2009

Related U.S. Application Data

(63) Continuation-in-part of application No. 11/707,783, filed on Feb. 15, 2007, now Pat. No. 7,384,145.

(60) Provisional application No. 60/774,097, filed on Feb. 16, 2006.

(51) Int. Cl.
*A61B 13/00* (2006.01)
*A61B 5/04* (2006.01)

(52) U.S. Cl. ........ 600/558; 600/372; 600/382; 600/383; 600/393

(58) Field of Classification Search ............ 600/558, 600/300, 308, 372, 382, 383, 393, 400, 406, 600/546, 547, 554, 561, 587; 351/219, 205, 351/221, 246; 702/189
See application file for complete search history.

(56) References Cited

U.S. PATENT DOCUMENTS

| | | | |
|---|---|---|---|
| 4,109,648 A | 8/1978 | Larke et al. | |
| 4,131,113 A | 12/1978 | Fender et al. | |
| 4,386,831 A | 6/1983 | Grounauer | |
| 4,874,237 A | 10/1989 | Cringle | |
| 5,297,554 A | 3/1994 | Glynn et al. | |
| 5,506,633 A | 4/1996 | Sperling | |
| 5,886,769 A | 3/1999 | Zolten | |
| 6,688,746 B2 | 2/2004 | Malov | |
| 7,018,040 B2 | 3/2006 | Blum et al. | |
| 7,037,943 B2 | 5/2006 | Peyman | |
| 2003/0149350 A1 | 8/2003 | Porciatti | |
| 2003/0158497 A1 | 8/2003 | Graham et al. | |
| 2004/0039298 A1 | 2/2004 | Abreu | |
| 2004/0106965 A1* | 6/2004 | Chow ............................. 607/54 |
| 2005/0119544 A1 | 6/2005 | Valjakka et al. | |

* cited by examiner

*Primary Examiner* — Jeffrey G Hoekstra
(74) *Attorney, Agent, or Firm* — Olson & Cepuritis, Ltd.

(57) ABSTRACT

The present invention provides an electrode array device for simultaneously detecting electrical potentials at five or more locations on the anterior surface of an eye. The device comprises a dielectric lens substrate having a concave inner surface conforming to the anterior surface of the eye, and at least five recording electrodes positioned in relation to the inner surface of the lens substrate so as to make electrical connection with the anterior surface of the eye when the lens substrate is placed on the anterior surface of eye. Each recording electrode is in electrically conductive communication with a corresponding conductive contact, there being one conductive contact for each recording electrode. Each conductive contact is adapted for operable connection to signal processor, and each conductive contact is electrically insulated from the anterior surface of the eye. A computational method for analyzing electrophysiological potentials recorded at five or more locations on the anterior surface of the eye, which reflect the spatial distribution of activity of the retina, is also provided.

19 Claims, 11 Drawing Sheets

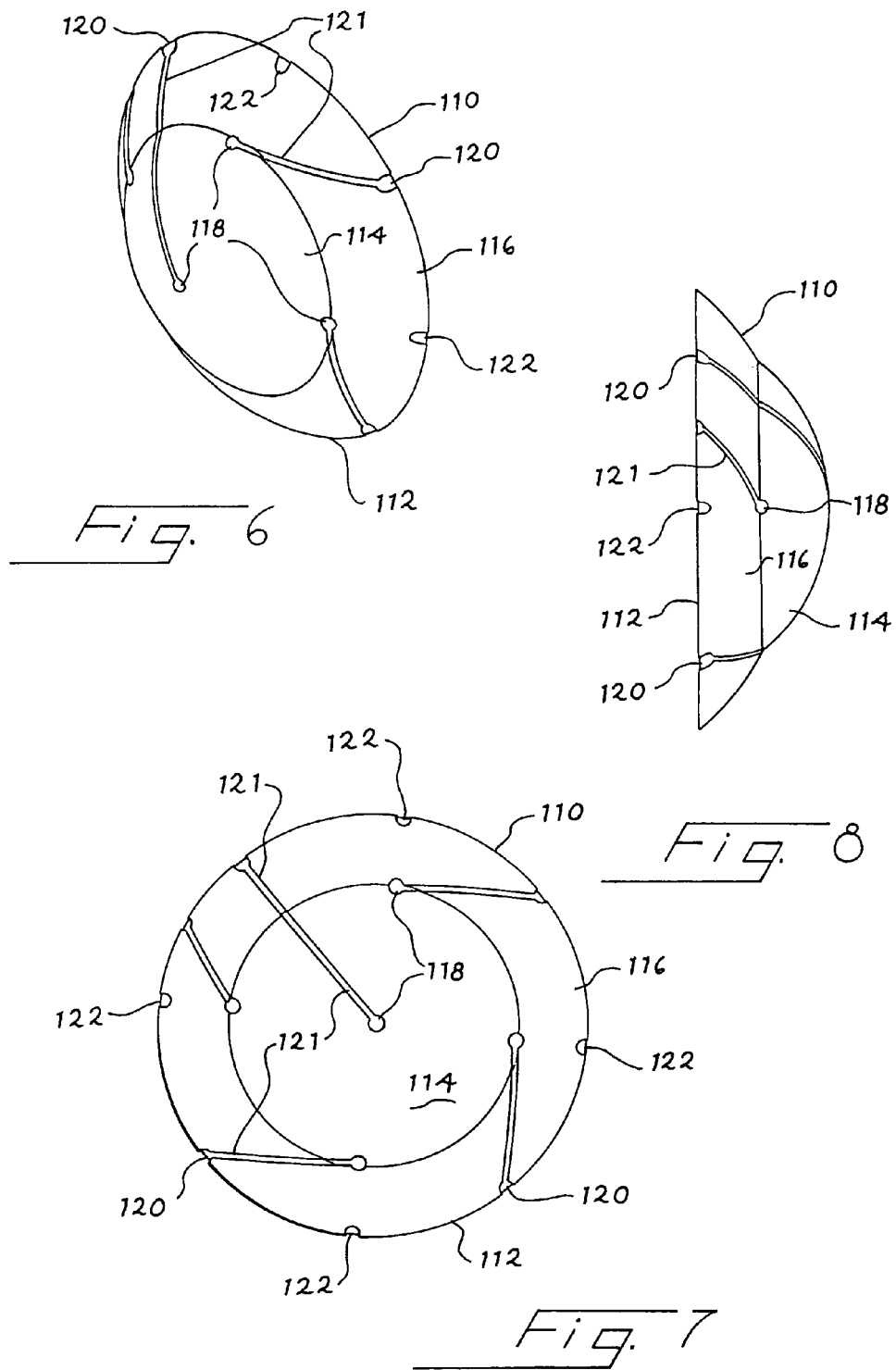

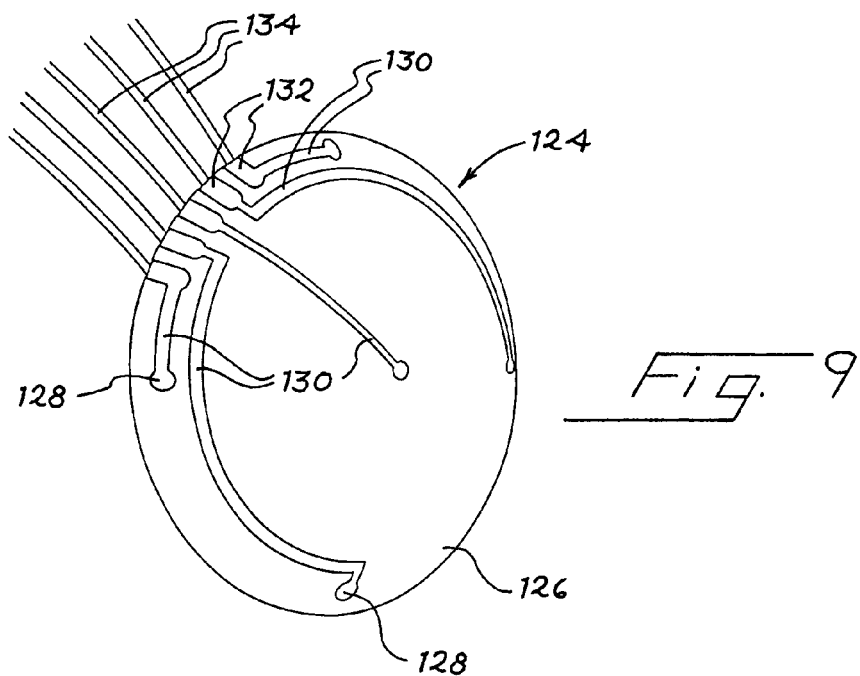
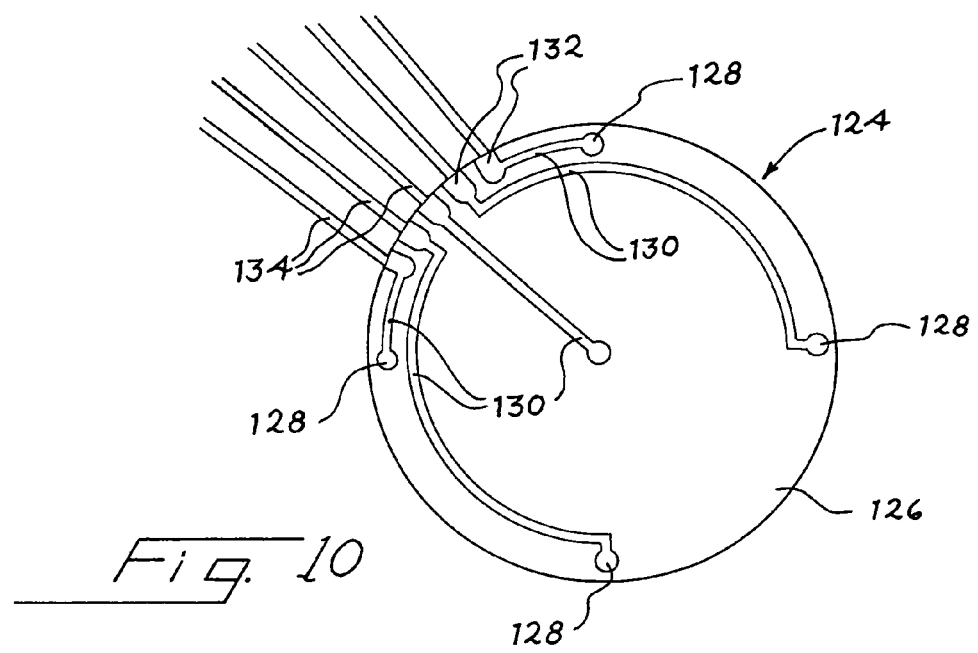

US 8,118,752 B2

APPARATUS AND METHODS FOR MAPPING RETINAL FUNCTION

CROSS-REFERENCE TO RELATED APPLICATIONS

This application is a continuation-in-part of U.S. Ser. No. 11/707,783, filed on Feb. 15, 2007, now U.S. Pat. No. 7,384, 145, which claims the benefit of U.S. Provisional Application for Patent Ser. No. 60/774,097, filed on Feb. 16, 2006, each of which is incorporated herein by reference in its entirety.

FIELD OF THE INVENTION

The present invention relates to electrophysiological neuroimaging, also referred to as surface potential mapping, specifically as applied to the eye. More specifically, this invention relates to apparatus and methods for simultaneously determining electrical potentials at multiple locations on the surface of the eye, and for using the so-determined measurements of electrical potentials to calculate the magnitude of neural activity at specific locations on the retina. The resulting data can be used to map retinal activity, and can be used to study, diagnose, or monitor the progression of ocular diseases. The apparatus and methods described here comprise the novel technique of multi-electrode electroretinography (meERG).

BACKGROUND

Measurement of the function of the retina, either directly or indirectly, is a central component in diagnosing, assessing and monitoring the progression of dysfunction due to disease or trauma. Indirect measurements of the function of the retina include psychophysical tests, e.g. the Humphrey Visual Field test. Direct measurements include electrophysiological measurements such as the electroretinogram (ERG).

Dysfunction of the retina due to disease or trauma is often localized. Further, early detection is of critical importance in cases of potentially blinding eye diseases, as treatments are directed to slowing or halting progression of vision loss. Therefore, measurement of the function of the retina at defined spatial locations on the retina is of great interest.

The Humphrey Visual Field test results in a map of perceptual quality arising from different areas of the retina. However, this psychophysical test has several drawbacks including difficulty in administering the test to young patients or patients with very low vision, and the fact that it measures quality of visual perceptions, and does not directly reflect function at the retina. Further, such psychophysical tests cannot be administered to animals.

The non-invasive measurement of body surface potentials for the purpose of analyzing the bioelectric activity of nerve and muscle tissue has been a known technique in research and clinical environments for many decades. The most common recording strategy for body surface potentials is to use a differential amplifier (FIG. 1). To use a differential amplifier, three electrodes are employed, referred to as the active or recording electrode, the reference electrode, and the ground electrode.

In practice, the recording electrode is placed on the body surface at a position overlying the internal bioelectric tissue of interest, e.g. the heart or the sciatic nerve, with the understanding that the surface potentials reflecting the bioelectric activity of the tissue of interest will be strongest at that location. The potentials recorded at this location will therefore be comprised of the desired signal (potentials related to bioelectric activity of the tissue of interest) plus undesired noise (due to other bioelectric tissues in the body, motion artifacts, or exogenous sources such as nearby power lines).

The reference electrode is placed on the body surface at a location near to, but some distance away from, the active electrode, with the understanding that the body surface potentials recorded at this location will consist of primarily noise similar to the noise recorded by the active electrode, and with the further understanding that the contribution of the bioelectric activity of the tissue of interest to the these recorded potentials will be negligibly small. Therefore, this electrode will record noise only.

The ground electrode is placed on the body surface very distant from the active and reference electrodes, and is used to connect the body to earth ground, which serves as a reference potential, generally taken to be zero Volts.

Referring to FIG. 1, amplifier 10 includes a recording electrode input 14, a reference electrode input 16, a ground electrode input 18, and an output 20. The potentials recorded by the electrodes connected to inputs 14, 16, and 18 are $E_a$, $E_r$, and $E_g$, respectively. $E_{out}$ is the potential at the output 20 of differential amplifier 10, and G is the gain of differential amplifier 10. Differential amplifier 10 performs the following algebraic operation on these potentials: $E_{out}=[(E_a-E_g)-(E_r-E_g)] \times G$.

Because the ground electrode is connected to earth ground and taken to be zero volts, this operation can be simplified as: $E_{out}=[(E_a)-(E_r)] \times G$; or, equivalently: $E_{out}=[(signal+noise)-(noise)] \times G$, which reduces to: $E_{out}=[signal] \times G$.

Thus, the output of differential amplifier 10 is the difference in potential between the active and reference electrodes, multiplied by the amplifier gain. The tremendous advantage of the differential amplifier over single-electrode recording is the subtraction of noise from the signal recorded by the active electrode before the gain is applied. $E_{out}$ is therefore a single potential (or time series of potentials) that is directly related to the underlying bioelectric activity of the target tissue.

Differential amplifier recording is used universally to record the corneal electroretinogram, or ERG. The ERG is a recording of the surface potential at the cornea (transparent portion of the anterior eye), which reflects the underlying bioelectric activity of the neural retina. The ERG is recorded with a number of specific electrode designs.

Some ERG electrodes are monopolar, meaning that only the active electrode contacts the eye surface. However, even monopolar electrodes are used in conjunction with differential amplifiers due to the advantage afforded by these amplifiers of subtracting noise from the signal recorded by the active electrode. Therefore, when using monopolar ERG electrodes, the reference electrode is a skin surface electrode placed on the face near the eye. One example of a monopolar contact lens ERG electrode includes a plastic lens substrate, a single gold foil active electrode, and a single wire, which connects the active electrode to a differential amplifier such as that shown in FIG. 1.

The most common type of ERG electrode is a bipolar design, in which both the active and reference electrodes contact the eye. The most common example of a bipolar ERG electrode is the Burian-Allen contact lens electrode, which includes an active ring-shaped electrode integral to a clear plastic contact lens. An opaque speculum is used to hold the eye lids open and also supports the reference electrode on its lower surface. A twisted pair of wires connects the active and reference electrodes to a differential amplifier. A second type of bipolar ERG contact lens electrode is the Doran GoldLens. This contact lens electrode includes two gold foil ring-shaped electrodes on the inner surface of a contact lens substrate. The electrodes directly contact the corneal surface. Each ring of gold foil is connected to a wire, which in turn connects to a differential amplifier. The ground electrode is typically a skin surface electrode placed on the face or earlobe.

A third example of a bipolar ERG contact lens electrode is described by Grounauer (U.S. Pat. No. 4,386,831), as shown in FIG. 2, which illustrates the connections of the active and reference electrodes to the positive (+) input 14 and negative (−) input 16 of the differential amplifier 10. The design described by Grounauer is a contact lens with four plastic pins 46 protruding from the front surface (see Column 2, lines 10-13; and FIG. 3 of Grounauer). The primary purpose of pins 46 is to hold the eyelids open during an ERG recording session. One of the pins has an axial bore-hole 44, which accepts a metal wire or rod to serve as the active electrode 42 (see Column 2, lines 14-15; lines 18-20; and FIG. 2 of Grounauer). A second pin is used to wrap a wire 40 around, which will then contact the lower eyelid and serve as the reference electrode (see Column 2, lines 46-59 of Grounauer). These two wires (40, 42) would then be connected to a differential amplifier 10 in the typical manner, as described above, resulting in one conventional ERG signal at the amplifier output 20.

A fourth example of bipolar electrodes used for ERG recording is described by Porciatti (US 2003/0149350A1), as shown in FIG. 3, which illustrates that for each eye 48, one active electrode 50 beneath each eye 48 is connected to the positive input 14 of a differential amplifier 10, and one reference electrode 52 above each eye 48 is connected to the negative input 16 of a differential amplifier 10. Both amplifiers 10 are connected to the same ground electrode 54, on the forehead. Porciatti describes the use of two bipolar electrode pairs to measure the ERG from both eyes simultaneously (see FIG. 1 of Porciatti). Both bipolar pairs of electrodes are referenced to a single ground electrode (see FIG. 1 of Porciatti). Thus, five electrodes are used to perform two simultaneous ERG measurements. The method of Porciatti differs from most ERG measurement techniques in that Porciatti places the active and reference electrodes on the skin surface just below, and just above, the eye, respectively. Porciatti recognizes that by placing the active and reference electrodes at this distance from the bioelectric tissue of interest, namely the retina, that the signal amplitude recorded will be reduced (see paragraph 0022 of Porciatti). Each bipolar pair of electrodes, consisting of one active electrode and one reference electrode, would be connected to a differential amplifier, resulting in one conventional ERG signal per eye.

There are many variations of the ERG technique that are distinguished by the type of stimulus used; some of these variations are the pattern ERG (pERG), multi-focal ERG (mfERG), paired-flash ERG, focal ERG, flicker ERG, photopic ERG, and scotopic ERG. All of these variations use one active electrode, one reference electrode, and a differential amplifier. All of these variations result in one conventional ERG signal at the output of the differential amplifier.

The common feature of all ERG recording described above is that a single ERG voltage signal is obtained from the differential amplifier, which represents the summed activity of the entire retina. It has long been known that the potentials on the eye surface resulting from bioelectric activity of the retina are not spatially uniform. Thus, the magnitude, and possibly the kinetics, of the recorded potential can be influence by the position of the active electrode. This is seen as a complication to ERG recording, and is usually mitigated by using an active electrode that contacts the eye surface over an extended area. The ubiquitous Burien-Allen contact lens electrode, as described above, uses gold foil rings concentric with the pupil as the active and reference electrodes. By contacting the eye surface at several points subtended by the ring, the spatial differences in potential on the eye surface are effectively averaged out via electrical shunting by the gold electrode. Thus, spatial differences in eye surface potentials are effectively ignored in all conventional ERG recording.

There is one example of exploiting the spatial differences in ERG potentials on the eye surface, for the purpose of detecting asymmetry in the eye surface potentials, which may then be taken to indicate an asymmetry in retinal activity as might be associated with retinal injury or disease. Cringle (U.S. Pat. No. 4,874,237) describes the use of four pairs of bipolar electrodes (see FIGS. 1 and 5 of Cringle) contained in a ring, such that the electrodes contact the sclera, peripheral to the cornea, but not the cornea itself. Each bipolar electrode pair may consist of one active electrode in contact with the sclera (white part of eye surface peripheral to the transparent cornea) (see FIGS. 1-4 of Cringle) plus one reference electrode attached to the forehead or cheek (see Column 2, lines 66-68 of Cringle). Alternatively, each bipolar pair may consist of one active electrode plus one reference electrode, which are both in contact with the sclera, positioned along a common radial line extending from the pupil center such that one electrode is located near the corneal margin, and one is slightly more peripheral to the corneal margin (see FIGS. 5-8 of Cringle). In either configuration, there are only four active electrodes in contact with the eye surface, and those four electrodes are confined to the sclera and specifically do not contact the cornea (see Column 1, lines 55-66; Column 2, lines 63-66; Column 4, lines 12-16; Column 4, lines 60-67 of Cringle). In this way, each bipolar pair of electrodes is connected to one differential amplifier, resulting in one ERG signal that is specific to one position on the eye surface. Thus, four distinct ERG signals result.

Cringle then describes taking a further differential measurement between the signals derived from opposing active electrodes (see Column 2, lines 5-9; an FIGS. 1, 2, 5, 6 of Cringle). Thus, two difference signals are produced, where the magnitude of each difference signal is related to the asymmetry in potentials recorded along the specified axis. If the potentials are symmetrical along a given axis, the difference signal along that axis will be zero (see Column 3, lines 13-18 of Cringle). Any non-zero difference indicates an asymmetry in retinal activity along that axis (see Column 3, lines 19-25 of Cringle). However, for any non-zero difference in eye surface potential along one axis, there are an infinite number of possible distributions of underlying retinal activity that could result in that difference. Therefore, the size and location of a retinal lesion cannot be determined using the method proposed by Cringle.

Further, for a retinal lesion located at the center of the retina, as is typical in age-related macular degeneration, the most common cause of blindness in the U.S., the potentials recorded by Cringle's opposing pairs of electrodes would be similar, and thus the presence of the lesion would not be reflected in the output of the amplifiers. The method described by Cringle therefore cannot be used to obtain a map of retinal activity, which would indicate the location and magnitude of any arbitrary retinal lesion. In summary, the method described by Cringle uses four active electrodes on the sclera to detect only asymmetry in retinal activity.

While Cringle indicates that the disclosed approach will provide information about the size and location of a retinal lesion (see Column 4, lines 37-40; Column 4, lines 67-68 of Cringle), no method that would actually provide information about the size and location of a retinal lesion is proposed or suggested. Theoretically, it is not even possible to obtain such location and size information from the output of the system described by Cringle, because the underlying computational problem is under-constrained. In such a system, the computational problem is referred to as the "inverse problem", in which the locations and magnitude of the underlying bioelectrical sources are solved for using the potentials measured at the eye surface. There simply is not enough information to make such calculations from the type of data obtained by the method and apparatus of Cringle, as explained below.

The distribution of retinal activity can be represented as a distribution of bioelectric dipoles. Each dipole is a vector, which has a position in three dimensional space (e.g., spatial coordinates x, y, z), a direction in three dimensional space (e.g., vector components Dx, Dy, Dz), and a magnitude (M). Since there are seven values required to mathematically describe each dipole (i.e., seven unknowns), it follows that at least seven measurements must be made to solve for the position, direction, and magnitude of each dipole. For the size and location of a retinal lesion to be determined with some degree of specificity, the retina must be divided into a number of equivalent dipoles regions, where each dipole represents the summed activity over a small area of retina. If a human retina is divided into 5 spatial units, each would be approximately 200 square millimeters ($mm^2$) in area and could locate the quadrant of the lesion or its presence at the central region of the retina. To represent each unit by one equivalent dipole, there would be a total of five dipoles, and 5×7=35 unknown quantities to solve for. Similarly, dividing the retina into 100 spatial units, each would be approximately 10 $mm^2$ in area. To represent each of the 100 units by one equivalent dipole, 700 unknown quantities must be determined at the eye surface. If fewer measurements are made, the computational problem will be under-constrained, and a solution cannot be obtained, since the number of measured quantities must always be at least equal to the number of unknown quantities in order to achieve a unique solution to the inverse problem. The methodology described by Cringle measures only 16 quantities (the x, y, z position for each of four active electrode, and the magnitude, M, for the potential at each electrode location). This number of measurements is sufficient only to solve for two equivalent dipoles, which represent the two axes of the retina subtended by the active electrode pairs. These two equivalent dipoles can only reveal asymmetry in the overall retinal activity along these axes, and nothing more. It is impossible to determine the size and location of a retinal lesion from the information provided by Cringle's four scleral measurement locations. Nowhere in the Cringle patent is this problem acknowledged, and nowhere in the Cringle patent is any solution to the inverse problem mentioned. The simple difference measurements described by Cringle only determine the amount of asymmetry in the distribution of retinal activity, and cannot be used to determine the size and location of a retinal lesion.

Many protocols have been developed to directly measure activity of the retina at defined spatial locations using the ERG. These include the focal ERG and multi-focal ERG methods. These methods also have significant drawbacks. The focal ERG measures function only in the central retina, and many conditions of great clinical interest (potentially blinding conditions of high prevalence, e.g. retinitis pigmentosa or diabetic retinopathy) first present in the peripheral retina. The multi-focal ERG (mfERG) measures approximately the central 50 degrees of visual field. The mfERG takes several minutes to record, during which the subject must fixate on a small target, making it difficult to record from very young patients or patients with low central vision. Further, the mfERG signal is not a true bioelectric signal, and physiological interpretation of the signal remains a challenge.

As noted above, eye diseases often result in localized dysfunction of the retina. In a clinical setting, electroretinography is a useful, non-invasive procedure for determining retinal activity in which electrical potentials at the eye surface are measured upon exposing the retina to a light stimulus. These surface potentials result from activity generated by the retina in response to the stimulus. The electrical potential at a given position on the eye surface is not related to the activity of only one unique retinal position. Rather, the potential at a given position on the eye surface is the sum of contributions from activity of all portions of the retina. In conducting a typical ERG, a single electrode is positioned on the anterior surface of a subject's eye and a second electrode, usually referred to as an "indifferent" or reference electrode is positioned to complete an electrical connection with the patient's upper anatomy. The indifferent electrode may be placed, for example, in the mouth or may be electrically coupled to the subject's ear or other convenient locus for such connection. The retina is then exposed to a light source and, in response, generates one or more electrical signals, which are then studied. An ERG is a record of the resulting electrical signals.

Retinal illumination during an ERG may be conducted in a number of ways. For example, a first set of electroretinographic readings may be taken in normal room light. In a second step, the lights may be dimmed for a significantly long period of time (on the order of 20 minutes), and readings are taken while the subject's retina is exposed to a light source. That is, after prolonged period in a dark environment, electrophysiological readings are taken at the onset of retinal exposure to light, and for a time period shortly thereafter. For example, after a sufficient time for adaptation of the retina to the dark environment has passed, a bright flash may be directed to the subject's retina with electroretinogram readings being taken. Each electroretinogram reading will differ depending upon the light conditions to which the patient's retina is subjected. However, standard responses have been established for each type of test and various useful conclusions can be drawn from excursions from such standardized data. In each test, the retinal response to each illumination is typically in the form of a voltage versus time waveform. Different types of waveforms have been defined for normal retinal responses. It is expected in a healthy subject, for example, that an electroretinogram shows a-wave and b-wave patterns normal in shape and duration, with appropriate increases in electrical activity as the stimulus intensity is increased.

As indicated above, electrodes used to measure corneal potentials may be mounted on a contact lens for convenient application in an outpatient setting. Such an electrode typically measures summed activity from the entire retina. In general, the electrical changes caused by the different major cell types of the retina (e.g., rod and cone photoreceptors, bipolar cells, horizontal cells, amacrine cells, ganglion cells, and Muller cells) tend to overlap in time, thus complex and varying waveforms are observed. The most prominent wave is the b-wave and the height of this wave can provide an indication of the subject's sensitivity to the illumination source. Tests can be conducted with illumination sources of different spectral content, intensity, kinetics, spatial patterns and spatial contrast, etc., and the results can be studied to determine the state of the subject's ocular health.

Simplified electrical models of the eye have been described in the literature. The first analytical account of the electric fields generated by retinal activity was given by Krakau, *Acta Opthalmologica;* 1959; 36(11):183-207, who used analytical methods based on Helmholz's theory of electromotive surface to estimate the potentials at the corneal surface. The eye was modeling as a perfect sphere containing no intraocular structures. Krakau's model assumed radial symmetry, and thus the eye model was reduced to two dimensions.

Doslak, Plonsey and colleagues extended the work of Krakau by incorporating three major ocular structures, the sclera, cornea, and lens. The region defined in this model as the "sclera" actually represented the combined retina, retinal pigment epithelium, choroid and sclera. This group maintained the assumption of axial symmetry, and therefore reduced the model to two dimensions (see Doslak et al., *IEEE Trans. Biomed. Eng.;* 1980; 27(2):88-94; Doslak et al., *Med. & Biol. Eng. & Comp.,* 1981; 19:149-156). This work necessarily used a finite difference algorithm to solve Laplace's equation for the model. This model did include the R-membrane, which arises in the retinal pigment epithelium.

Job. et al., *Med. & Biol. Eng. & Comp.,* 1999; 37:710-719, extended the model of Doslak to three dimensions, including the same level of anatomical detail (sclera, cornea, and lens), and used a similar finite difference approach. Similar to the Doslak model, the neural retina or sublamina of the neural retina were not distinctly defined in terms of anatomy or electrical properties. The model region considered to represent the "sclera" actually represented the combined retina, retinal pigment epithelium, choroid and sclera.

Davey et al., *IEEE Trans. Biomed. Eng.;* 1988; 35(11):942-7, modeled the eye as a two-dimensional oval of uniform conductivity. This model had only three regions defined by distinct electrical properties: the eye, the medium in front of the eye and the medium behind the eye. No intraocular structures were included in the model. The simplified geometry was required in order to implement the analytical methods used.

SUMMARY OF THE INVENTION

The present invention provides an electrode array device for simultaneously detecting electrical potentials at five or more locations on the anterior surface of an eye. The electrode array device comprises a dielectric contact lens substrate, e.g., a suitable polymeric material such as poly(methyl methacrylate), having a concave inner surface conforming to the anterior surface of the eye, and at least five (5) recording electrodes positioned in relation to the inner surface of the lens substrate so as to make electrical connection with the anterior surface of the eye when the lens substrate is contacted with or placed on the anterior surface of eye. Each recording electrode is in electrically conductive communication with a corresponding conductive contact pad, there being one conductive contact pad (or "contact") for each active electrode. Each conductive contact is electrically insulated from the anterior surface of the eye, and is adapted for operable connection to a signal processor that preferably includes an amplifier and is capable of detecting and amplifying an electrical potential signal from each electrode. Preferably, the lens substrate includes 5 to 500 recording electrodes. The electrodes and contact pads can be made from a metal, such as a noble metal (i.e., a corrosion resistant metal of groups VIIb, VIII, and Ib of the second and third transition series of the periodic table, preferably gold, platinum or iridium), as well as from a conductive polymer, or a semiconductor material (e.g., a doped silicon). If desired, the lens can include an integral vacuum port or line so that a mild negative pressure can be applied to the undersurface of the lens, to help anchor the lens to the surface of the eye, and prevent movement during measurement of electrical potentials on the eye surface.

In some preferred embodiments, each recording electrode comprises a conductive material (e.g., a noble metal) deposited on the interior surface of the lens substrate. Preferably, each conductive contact pad is positioned in a peripheral region of the lens substrate, and is connected to its corresponding recording electrode via an electrically conductive trace (e.g., a metallic film or wire) that is electrically insulated from the surface of the eye.

In other preferred embodiments, each recording electrode comprises a cylindrical through-hole formed in the lens substrate adjacent to an un-insulated portion of its corresponding conductive trace. An electrically conductive connection is made between the conductive trace and the anterior surface of the eye when the lens substrate is fitted on the anterior surface of eye in the presence of an amount of a conductive liquid or hydrogel (i.e., a liquid or hydrogel made electrically conductive by inclusion of one or more electrolytes) sufficient to fill each through-hole and connect with the un-insulated portion of the trace. Non-limiting examples of conductive liquids include saline or natural tears. Non-limiting examples of conductive hydrogels include water swellable salts of poly(carboxylic acid) materials such as crosslinked poly(acrylic acid) salts, carboxymethylcellulose salts, agar, alginate, collagen, and the like. Each through-hole can be fully or partially lined with a conductive material, such as a noble metal, in electrically conductive contact with the conductive trace, if desired. In other embodiments, each electrode comprises a conductive wire passing through the contact lens substrate (e.g., either embedded in the substrate or positioned within a through-hole).

In some embodiments, the lens substrate is configured to provide corrective refractive power to correct for defects in the visual acuity of the eye, while in other embodiments, the lens substrate has neutral refractive properties, or the lens substrate is plano-concave.

In another useful embodiment, the electrode array device includes one or more scleral recording electrodes positioned to make electrical connection with the sclera of the eye when the lens substrate is fitted to or placed on the anterior surface of the eye. Each scleral electrode is in electrically conductive communication with a corresponding conductive scleral electrode contact pad, which is electrically insulated from the anterior surface of the eye, there being one scleral electrode contact for each scleral electrode. Each scleral electrode contact is adapted for operable connection to a signal processor as described above. Preferably, each scleral electrode contact is positioned in a peripheral region of the lens substrate, and can be connected to its corresponding scleral electrode via an electrically conductive trace that is electrically insulated from the surface of the eye. Alternatively, the contact can be directly connected to the electrode.

In some preferred embodiments, each scleral electrode comprises a cylindrical through-hole formed in the lens substrate adjacent to an un-insulated portion of its corresponding conductive trace. In such embodiments, an electrically conductive connection is made between the contact pad and the anterior surface of the eye when the lens substrate placed on the anterior surface of eye in the presence of an amount of a conductive liquid or hydrogel sufficient to fill each hole and connect with the un-insulated portion of the trace or directly connect with the contact pad, as the case may be.

Preferably, the electrode array device of the invention is utilized in an electroretinographic (ERG) system. An ERG system of the present invention comprises an electrode array device of the invention, comprising a plurality of recording electrodes on or integral with a lens substrate, in which each electrode thereof is in electrically conductive communication with a signal processor (e.g., a signal sensing and recording device) capable of detecting and amplifying the signals from the electrodes. The signal processor generally includes an amplifier for each electrode, and optionally is incorporated in a computer, such as a special purpose or general purpose computer (e.g., a microprocessor device, a personal computer, and the like). The signal processor preferably is capable of processing the electric potential signals obtained from the ERG measurements in a form suitable for data analysis. The signal processor also preferably includes or can be interfaced with a data storage device (e.g., random access memory, hard drive storage, and the like) and optionally includes or can be interfaced with a display device for displaying some or all of the recorded electrical potentials, e.g., in the form of numerical tables, individual electroretinographs, or as a map of retinal activity, as desired. Preferably, the electrical potential data recorded from each electrode is stored in a manner such that the data can be individually accessed and/or analyzed, and which can be combined with electric potential data from one or more other electrodes, as desired, e.g., for noise reduction purposes. In some embodiments, a computer is programmed to generate a map of retinal activity from the electric potential data.

In another aspect, the present invention provides a method for simultaneously recording electrical potentials from five or more locations on the anterior surface of the eye of a subject. The method comprises contacting the anterior surface of the eye with an electrode array device having at least five recording electrodes and recording an electric potential signal from each electrode. The electrode array device comprises a dielectric lens substrate having a concave inner surface conforming to the anterior surface of the eye. The substrate includes at least five recording electrodes positioned in relation to the inner surface of the contact lens substrate so as to make electrical connection with the anterior surface of the eye, preferably at least the cornea). Each electrode is electrically connected to a signal processor as described herein.

In another aspect, the present invention provides a computational method for analyzing electric potentials recorded at the surface of the eye, which reflect activity of the retina. The method comprises determining underlying spatially differentiated retinal electrophysiological activity in the retina by comparing recorded eye surface potential data to estimated eye surface potentials obtained from a computational model of electrical properties of the eye. The model incorporates electrical parameters and dimensions for multiple ocular structures, including at least the tear film, cornea, aqueous humor, lens, vitreous humor, retina, R-membrane, sclera, and extraocular adipose tissue. The recorded eye surface potential data comprises at least five spatially differentiated electrical potential signals simultaneously recorded at predetermined electrode positions on the anterior surface of the eye with an array of recording electrodes (e.g., monopolar or bipolar, active electrodes). Preferably, the model comprises a plurality of spatially distributed nodes, subsets of which correspond to anatomical structures within the eye. The retina in the model preferably is subdivided into a plurality of spatially distinct retinal "source areas" equal or greater in number to the number of recorded potentials, wherein each source area comprises one or more nodes. Surfaces within each retinal source area, or subsets of source areas, have an assigned voltage, current, or charge magnitude depending on the type of cell or neural pathway under analysis. One preferred step in the method comprises applying a transfer matrix to the electrical potential at each electrode position on the anterior surface of the eye. The transfer matrix is obtained from the model and relates the electrical potential contribution of each retinal source area to a first set of designated source area magnitudes to provide a first set of estimated eye surface potentials.

The elements or weighting factors of the transfer matrix are obtainable by assigning a finite value to one node or a subset of nodes and assigning a null value to all the other nodes, and then calculating the electric potential contribution of that node or subset of nodes to each electrode position. Next, this process is repeated, so that each node or subset of nodes is iteratively given the finite value, and the electric potential contribution of each node or subset of nodes is calculated for each electrode position on the surface of the eye. This process ultimately provides a first set of estimated eye surface potential magnitudes, which represents the relative eye surface potential distribution that would result from a retina having essentially uniform electric potential activity. The set of finite values used to determine this distribution of relative eye surface potentials may vary from location to location, and thus reflect known anatomical distribution of cell types within the retina.

In a preferred embodiment, when the number of retinal source areas is equal to the number of recorded eye surface potentials, the system of equations represented by the measured potentials, the transfer matrix, and the unknown retinal source area magnitudes can be solved using standard linear algebraic methods, resulting in values that represent the magnitude of activity at each retinal source area.

In another preferred embodiment, when the number of retinal source areas is equal to or greater than the number of recorded potentials, the method includes the additional steps of calculating an error term representing the difference between the estimated eye surface potential and the measured eye surface potential at each electrode position. The differences between the estimated eye surface potentials and the recorded eye surface potentials are computationally minimized by iteratively changing the first set of designated source area magnitudes and recalculating the error term until the error term at each position is below a predetermined maximum value or is at a minimum value. This process provides a final set of retinal source values that collectively represents a map of the electrical activity (e.g., electrical potential or current) of the retina. The method may utilize reasonable constraints on the values of retinal source area magnitudes as may be determined from knowledge of physiology or which are gained from ophthalmic exam using other technology. For example, a known blind-spot or other instance of known retinal dysfunction may be used to restrict the value of one or more retinal source areas to a range of values appropriate for the level of dysfunction.

The method also can include the optional step of displaying the final set of retinal source values in correct anatomical relation to the retina to provide a graphical map of spatial differences in retinal activity of the subject eye. The final set of retinal source values can be displayed, for example, as predefined colors or shades of a single color, where each color or shade represents a magnitude or range of magnitude of an electrophysiological potential. All or part of the final set of source area magnitudes can also be displayed in registration with an image of the retina obtained using a different technology, such as fundus photography, fluorescence angiography, magnetic resonance imaging, or optical coherence tomography.

BRIEF DESCRIPTION OF THE DRAWINGS

FIG. 6 shows a perspective view of another contact lens assembly according to principles of the present invention.

FIG. 7 shows a front elevational view of the lens assembly of FIG. 6.

FIG. 8 shows a side elevational view of the lens assembly of FIG. 6.

FIG. 9 shows a perspective view of a further contact lens assembly according to principles of the present invention.

FIG. 10 shows a front elevational view of the lens assembly of FIG. 9.

FIG. 12A shows a top plan view and FIG. 12B shows a side cross-section.

FIG. 14A shows a top plan view and FIG. 14B shows a side cross-sectional view.

FIG. 15B shows an interface cable.

FIG. 16A shows an exploded side view of the lens and a partial cut-away side view of an eye, while FIG. 16B shows an exploded perspective view of the lens and a partial cut-away perspective view of the eye.

FIG. 18A shows a retina of uniform, normal activity, partitioned into individual source areas, and FIG. 18B shows a retina with areas of subnormal activity.

DETAILED DESCRIPTION OF PREFERRED EMBODIMENTS

Figure 1:
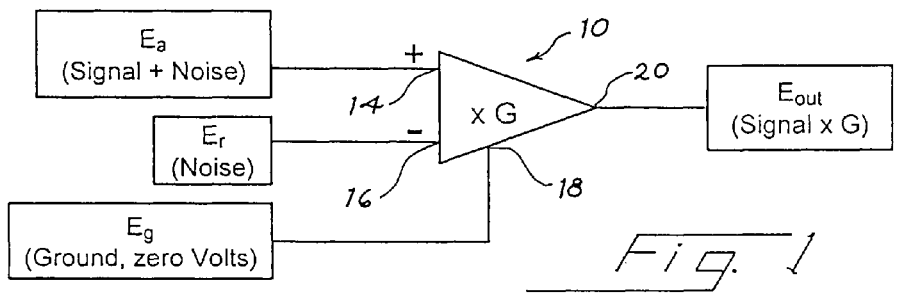
FIG. 1 shows a schematic representation of a differential amplifier.
Figure 2:
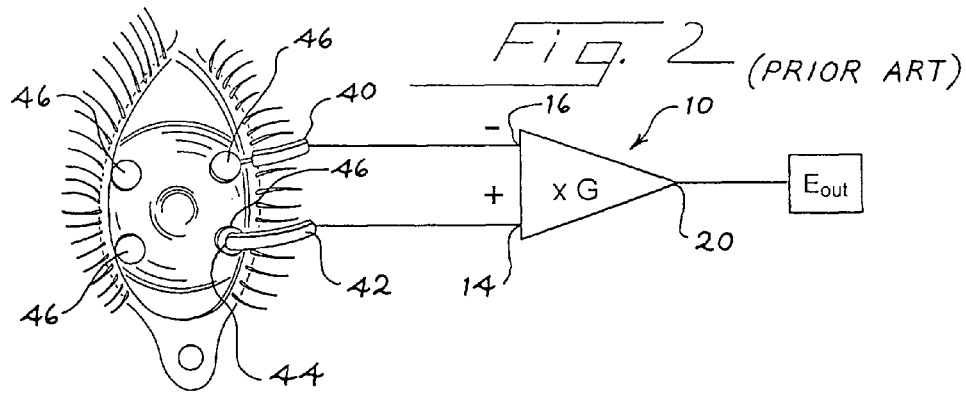
FIG. 2 shows a schematic representation of differential amplifier connected to a contact lens electrode as described by Grounauer.
Figure 3:
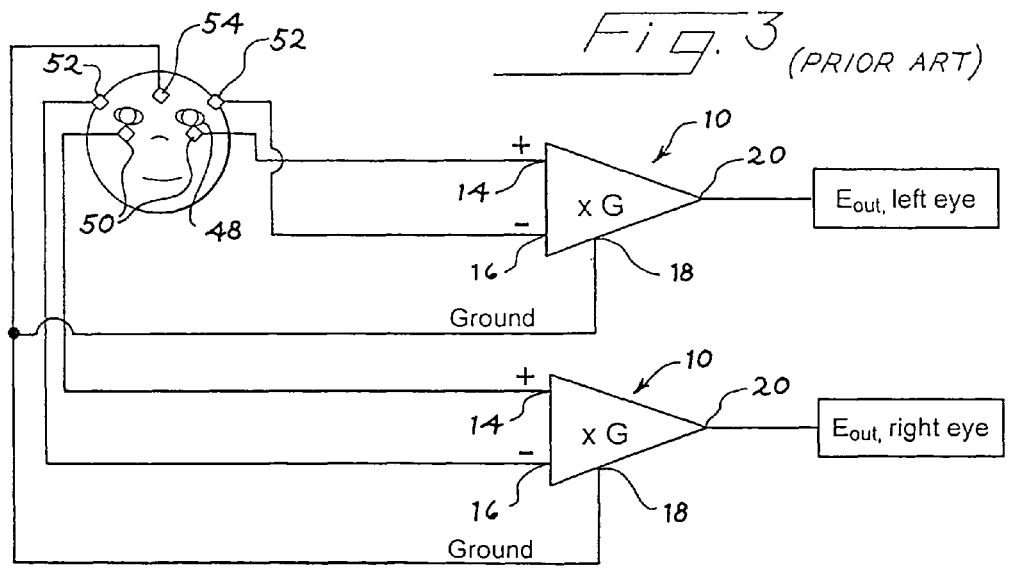
FIG. 3 shows an electroretinogram measurement technique as proposed by Porciatti, showing that for each eye, one active electrode placed beneath each eye is connected to the positive input of a differential amplifier, and one reference electrode placed above the eye is connected to the negative input of a differential amplifier. Both amplifiers are connected to the same ground electrode, placed on the forehead.

The invention described herein is, of course, susceptible of embodiment in many different forms. Preferred embodiments of the invention are shown in the drawings and described herein in detail. It is understood, however, that the present disclosure represents an exemplification of the principles of the invention and does not limit the invention to the illustrated embodiments. For ease of description, different arrangements embodying the present invention are described herein in their usual assembled position as shown in the accompanying drawings, and terms such as upper, lower, horizontal, longitudinal, etc. may be used herein with reference to this usual position. However, the arrangements may be manufactured, transported, sold or used in orientations other than that described and shown herein.

New systems and techniques are provided for simultaneously determining local bioelectrical activity in multiple locations on the retina and, if desired, may be used with existing techniques.

The focal ERG and the multi-focal ERG methods are comprised of focal stimuli to the retina and recording the ERG signal from a single active electrode, at the eye surface. By contrast, the invention described herein uses a full-field, homogeneous, preferably spatially invariant stimulus and an array of recording electrodes placed on the eye and optionally the head. Surface potentials are recorded simultaneously from several locations on the eye and head, and these signals are then analyzed and interpreted to create a map of the signal source distribution across the retina. While this technique is analogous to functional brain mapping using an array of scalp electrodes to record the electroencephalogram, or functional cardiac mapping using an array of chest electrodes to record an electrocardiogram, applications of such methods to the eye is novel to the present invention.

It should be appreciated that the array of electrodes must be at least translucent, so that it can transmit at least some light from an external illumination source to the retina, but does not necessarily need to be transparent. The contact lens base of the electrode array may be partially opaque or appear cloudy due to significant light scattering, affording a translucent, but not transparent structure. A translucent array may preclude formation of a visual image on the retina, but still allows for sufficient light from the stimulus source to reach the retina and elicit a bioelectric response. Light scattering by a partially opaque or translucent contact lens electrode array could be advantageous in some instances in the multi-electrode electroretinography (meERG) techniques of the invention by providing a uniform illumination of the retina, thereby simplifying the design of the stimulating light source. For example, the electrode array can be formed from a translucent, cloudy material, or alternatively, the array can comprise very narrow (fine) or thin conductive elements that transmit a sufficient amount of light, while not necessarily being optically clear and transparent.

Figure 4:
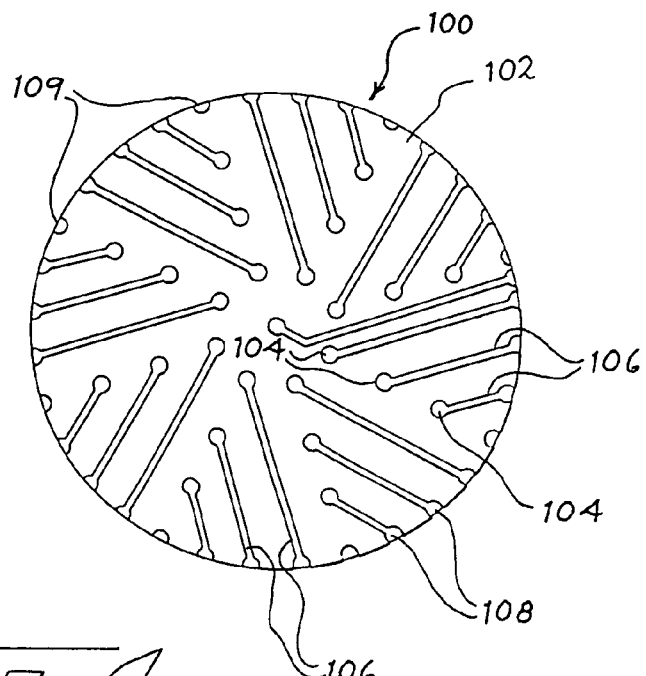
FIG. 4 shows a front elevational view of a contact lens assembly according to principles of the present invention.
Figure 5:
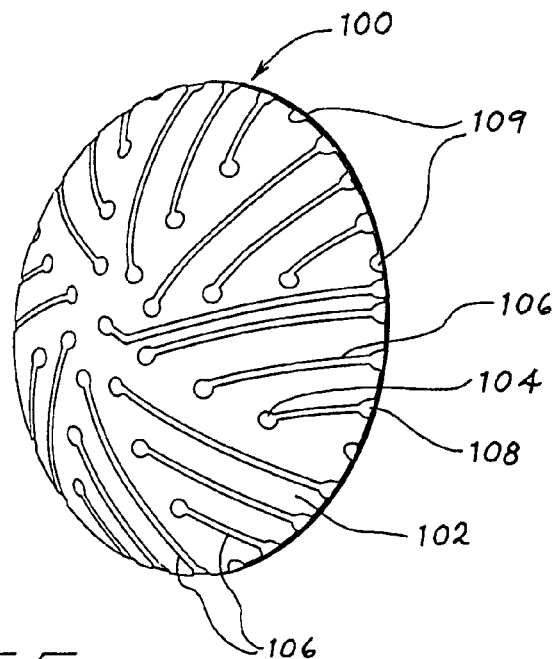
FIG. 5 shows a perspective view of the lens assembly of FIG. 4.

Referring now to FIGS. 4-11, corneal contact lens assemblies and systems according to principles of the present invention, useful for humans and other species, are shown. Referring to FIGS. 4 and 5, a corneal contact lens assembly 100 includes a corneal contact lens base 102, which is preferably constructed of known materials, such as poly (methyl methacrylate) (PMMA), using known techniques. Virtually any translucent material known today could be substituted as desired. The contact lens base can be plano-concave if desired, i.e., having one curved surface which contacts the surface of the eye and a planar surface facing away from the eye, which would aid in introducing certain optical stimuli to the retina by eliminating the refractive power of the cornea. The contact lens body 102 provides a transparent or translucent substrate for carrying a plurality of electrodes 104 applied to contact lens base 102 using known techniques, such as metal deposition. Electrodes 104 may vary in material of construction, including gold, platinum, iridium or other metals amenable to the fabrication process, or may be conductive polymers or doped silicon semiconductor materials, for example. As will be appreciated by those skilled in the art, contact lens assembly 100 can be scaled to virtually any size desired. The corneal contact lens assembly may be free to move relative to the cornea, or may be held in place by means of a speculum that extends under the eye lids, or by way of a vacuum applied through an integral vacuum port or catheter incorporated into the lens base.

As indicated in FIGS. 4 and 5, electrodes 104 are connected to conductive contacts 108 via conductive traces 106. Traces 106 preferably are relatively thin and are spaced apart so as to allow a substantial amount of light to pass through the lens assembly 100. Put another way, even with a plurality of electrodes 104 and traces 106, such as the 33 electrodes and traces shown in FIGS. 4 and 5, the contact lens assembly 100 allows a substantial amount of light to pass through. Contacts 108 are adapted for electrical connection to a signal processor and are positioned in a peripheral region of base 102. Additional electrodes 109 are also included around the periphery of lens 100. Electrodes 109 wrap around the edge of lens 100 so that the top of electrode 109 acts as its own contact point for connection to a signal processor.

If a substantially transparent lens is desired, the ability of light to pass the electrodes is due either to the thinness, and hence the transparency of the electrodes, or to their spacing, or both. If spacing is relied upon, it is important to note that because the electrode array on the contact lens is not in the focal plane of the eye, any shadows cast by opaque electrodes and conductive traces are blurred sufficiently at the surface of the retina so as to result in an approximately uniform decrease in retinal illuminance, which will not hinder the meERG approach of this invention. The conductive traces 106 may vary in material of construction, and may comprise, e.g., gold, platinum, iridium or other metals amenable to the fabrication process, or may be conductive polymers or doped silicon structures.

Referring to FIGS. 6-8, a contact lens assembly 110 includes a lens body 112 having an inner or central portion 114 and an outer concentric portion 116. Inner portion 114 has a smaller radius of curvature than outer portion 116. Inner and outer portions 114, 116 are dimensioned to contact the cornea and the sclera, respectively. In the illustrated embodiment, five active corneal electrodes 118 are provided, and extend to contacts 120 via conductive traces 121. Contacts 120 are adapted to provide an electrically conductive connection between corneal electrodes 118 and an electric signal processor device. Lens assembly 110 also includes four scleral electrodes 122 in the periphery of lens body 112, which are adapted to provide a direct connection to a signal processor (i.e., without need of a conductive trace). Each electrode 118 and 122 includes a portion that contacts the surface of the eye when in use. Conductive traces 121 are insulated from direct contact with the surface of the eye.

Referring to FIGS. 9 and 10, contact lens assembly 124 includes a contact lens body 126 carrying five integral electrodes 128. Four electrodes 128 are distributed along the peripheral region of lens body 126 and one electrode positioned in the center of lens body 126. Electrodes 128 are connected to contacts 132 via conductive traces 130. External wires 134 are connected to contacts 132 to provide a conductive connection to a signal processor for amplifying, filtering, or otherwise processing the electrical potential signals.

Figure 11:
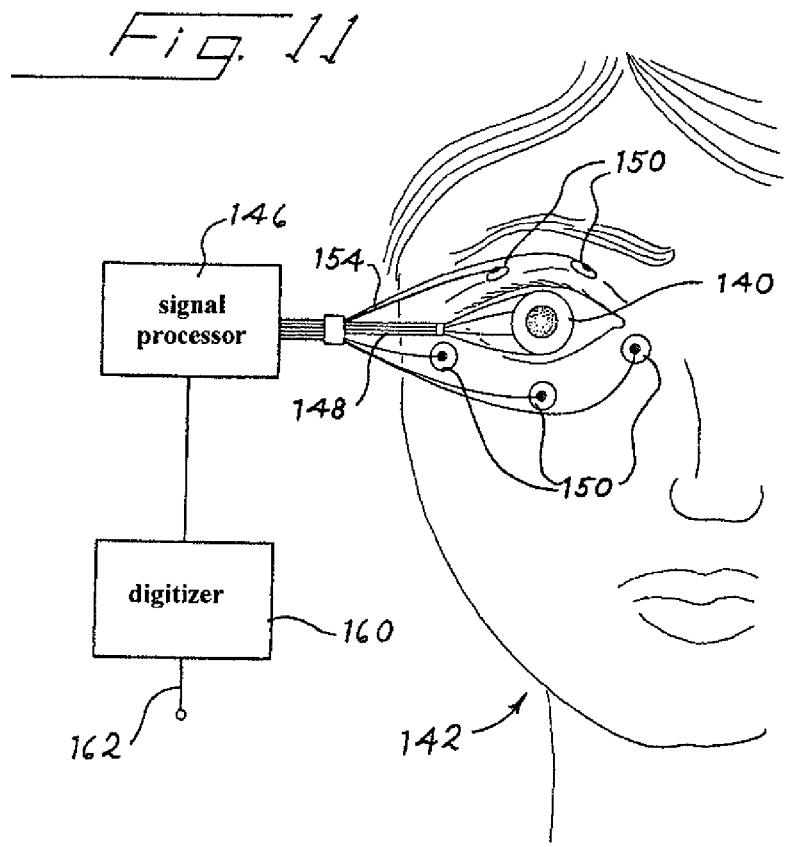
FIG. 11 shows a data collection system according to principles of the present invention.

Referring now to FIG. 11, a data collection system is shown in which a contact lens assembly 140 is fitted to a subject 142. The contact lens assembly may comprise any of the contact lens assemblies shown in FIGS. 4-10 herein, and preferably contains five or more electrodes coupled to a signal processor 146 by electrical leads 148. Five additional electrodes 150 are connected to portions of the skin surrounding the subject's eye. If desired, the skin electrodes can also be placed in contact with the scalp. Skin electrodes 150 are coupled to signal processor 146 by electrical leads 154. The electrodes and their connecting leads may be conveniently provided as a preassembled lead set, for use in the laboratory or in the field, as needed. Signal processor 146 contains filters and amplifiers appropriate for recording the electroretinogram, typically operating in a bandwidth of 0.1-500 Hertz, with a gain of 1000×. The processed signal(s) are preferably digitized at 160 for output on port 162 for storage and later analysis.

As can be seen from the above examples, electrodes are provided in the form of contact lens assemblies for electroretinographic recording at five or more sites simultaneously. Included is a contact lens body having an outer periphery, an inner surface facing the subject's eye and an opposing outer surface. An array of electrodes with conductive traces, preferably five or more, is carried on the inner surface of the contact lens body so as to form an integral combination therewith. Preferably, the conductive traces are narrow enough, and preferably thin enough, so as to transmit light from an illumination source to the retina, to provide a full-field stimulation of the subject's eye.

The array of electrodes is positioned about the contact lens body in a manner conducive to contacting the subject's cornea. If desired, the subject's sclera can also be contacted. It is generally preferred that the electrodes are connected to contact points at the outer periphery of the contact lens body via conductive traces, for electrically connecting the electrodes to electrical circuitry external to the electrode (e.g., a signal processor, computer, etc.).

Additional Points of Interest.

The present invention provides a number of notable improvements to prior systems and methods. For example, the present invention provides a computational method of using eye surface potentials to determine local retinal activity useful in employing the meERG system described herein. Further, the present invention provides a finite-element model useful in performing this computational task.

The meERG technique of the present invention can be employed in a cost effective manner, by utilizing any of the specialized photic stimuli typically used with standard ERG techniques. This novel use of these types of stimuli can be employed, for example, to provide information about function in specific retinal circuits or cell types, within spatially-defined regions of the retina, that is not available from existing methods.

The present invention provides a computational method used to calculate, approximate, or infer information about electrophysiological activity in the retina, especially spatial differences in such activity, based on measurements of electrical potentials made at the anterior surface of the eye. This computational method may include appropriate adaptations of any of the varied techniques developed for functional brain mapping based on electroencephalographic recordings, or those developed for mapping of cardiac activity based on measurements of cardiac potentials made at the surface of the heart or the torso, or any combination of elements of these techniques applied to solving for retinal potentials or currents based on knowledge of eye surface potentials. With this computational method, retinal activity is determined from measurements of eye surface potentials via an electrode array, as set out herein.

A finite-element model of the eye is provided, incorporating appropriate anatomical structures of the eye and surrounding tissues and materials, possibly including the contact lens electrode array described herein, and including the electrical properties of each structure in the eye. The model simulates retinal activity via a static distribution or time-varying change in charge distribution or local currents within or across the retina, used in the above-described computational method of determining retinal activity from measurements of eye surface potentials via an electrode array. This finite-element model of the eye can be used in the determination of the optimum design of the contact lens electrode array inherent in the meERG approach as described here.

The present invention is also directed to the use of known photic stimuli, which are designed to selectively elicit responses from specific cell types or functional pathways in the retina. These stimuli are used in conjunction with an array of eye surface measurement electrodes as described above, such that spatial differences in function of these cell types or functional pathways can be obtained.

A system and method are provided by the present invention for obtaining information about the spatial distribution of photoreceptor activity and neural activity in the retina using simultaneously recorded multiple biopotential signals. In one example, the information thus gathered is used to assess retinal dysfunction due to trauma or disease. The biopotential signals are recorded from the surface of the eye and head using a plurality of electrodes, including those integral to a contact lens, as explained above and shown in FIGS. 4-16. The biopotential signals are recorded before, during, and after the presentation of an optical stimulus to the subject eye. The recorded biopotential signals are then analyzed and interpreted to reveal the distribution of photoreceptor activity and neural activity across the retina. The analysis and interpretation of the biopotential signals is quantitative, and makes use of an electromagnetic model of the subject eye. The subject may be animal or human.

As can be seen from the above, the present invention, in certain aspects, employs a plurality of electrodes located on the anterior surface of the eye, or the eye plus face and/or scalp. The electrodes record biopotentials at the eye surface that result from retinal activity induced by a light stimulus. The recorded biopotentials are then used to infer the spatial distribution of physiological activity in the retina of the subject. Solving for the spatial location and magnitude of electromagnetic sources from knowledge of field potentials recorded some distance from the source is referred to herein as source modeling, or solving the inverse problem. This technique has been applied for decades for the purpose of functional brain mapping and functional cardiac mapping, and is well known for that purpose. Here, analogous recording and computational approaches are uniquely applied to the eye, as explained herein.

As mentioned, the present invention uses an array of recording electrodes integral to a contact lens, to record the electroretinographic biopotentials from the surface of the eye at multiple locations simultaneously. These eye-surface recordings may be augmented by additional surface potential recordings made from the face or scalp using conventional skin electrodes designed for this purpose.

Another aspect of the present invention is the quantitative approach used to infer the spatial distribution of physiological activity in the retina from the measured surface potentials. As mentioned, this approach uses a detailed finite-element model of the subject eye, containing the proper anatomical and electrical properties of all major ocular tissues, including the tear film, cornea, aqueous humor, lens, vitreous humor, retina, R-membrane, sclera, and extraocular adipose tissue. Such models have been constructed for human and rat eyes, and can be adapted in a known manner, to any species for which appropriate anatomical information is available.

The model can be used, for example, in several ways. First, a library of eye surface potential distributions can be generated by simulating different locations and degrees of retinal dysfunction, and then comparing the measured surface potentials to the library. The distribution from the library with the closest match to the to the recorded potentials represents an estimate of the spatial extent and degree of retinal dysfunction. Another approach is to apply any of the many mathematical methods developed for the analogous goals of mapping brain function or cardiac function. These methods are reviewed in He and Lian, Crit. Rev. Biomed. Eng. 2002; 30(4-6):283-306; and He and Wu, Crit. Rev. Biomed. Eng. 1999; 27(3-5):285-338.

With the present invention, a finite-element model is used to solve for the location and magnitude of retinal source contributions to surface potentials recorded on the eye surface or the eye and head. In contrast, previous attempts to relate spatial retinal potentials to spatial surface potentials used inadequate, very simple models and closed-form solutions to explore certain aspects of this field of research. Only the present invention relates spatial eye surface potentials to spatial retinal potentials using a substantially large number of surface electrodes. The spatial resolution of the solution for retinal source potentials is directly related to the number and distribution of measurement locations, and the invention described here is adapted for use with five to five hundred, or more, recording electrodes.

In a preferred aspect, the present invention provides a contact lens that contains a plurality of electrodes used to record ERG potentials at specific locations on the eye surface. The electrodes number between 5 and 500, depending on the size of the eye and the spatial resolution desired. Each recording electrode is electrically connectable to a signal processor (e.g., an amplifier or to a data acquisition input on a computer) by means of a wire, cable, or other conductive member. The electrodes may be any conductive material suitable for body surface recording, such as metals, doped silicon, or conductive polymers. The lens substrate may be any suitable transparent or translucent dielectric material, such as poly (methyl methacrylate) or other plastic, or materials typically used in the construction of soft contact lenses.

One embodiment consists of a contact lens of a diameter sufficient to subtend the subject's cornea (e.g., FIGS. 4, 5, 9, 10). The radius of curvature on the concave side is appropriate to fit the radius of curvature of the subject's cornea. The radius of curvature of the convex side is either equal to that of the concave side, or greater or less than that of the concave side, thereby producing a lens of neutral or corrective optical refraction. The electrodes are comprised of a thin layer of conductive material such as gold adhered to the concave side of the lens, possibly via an intermediate layer of material used to enhance the adhesion between the gold and the lens material. On the periphery of the lens, on the convex side, there exists one contact pad for each electrode. The contact pads are connectable to a signal processor (e.g., to amplifier inputs or a computer) via wires or other conductive cable. Each electrode preferably is connected to its corresponding contact pad by means of a conductive trace on the electrode, such as a thin layer of gold. The conductive trace extends from the electrode, across the concave side of the lens following a route that avoids other electrodes, and extends around the edge of the lens to the convex side, where it terminates at the contact pad. The gold adhered to the lens is electrically isolated from the eye surface everywhere except at the electrode locations and at the contact pads, by an insulating layer, such as a polyamide or Parylene (a polyxylene polymer).

A second embodiment is similar to that described above, but where the contact lens extends past the corneal margin (FIGS. 6, 7, 8, 14) onto the sclera. In this embodiment, a spherical section of lens material with radius of curvature appropriate to fit the subject's sclera extends the lens past the corneal margin. In this embodiment, this scleral extension contains a plurality of recording electrodes. The contact pads associated with each electrode are present on the convex surface of the scleral extension, and preferably are connected to each electrode by way of an insulated conductive trace as described above.

Figures 12A, 12B:
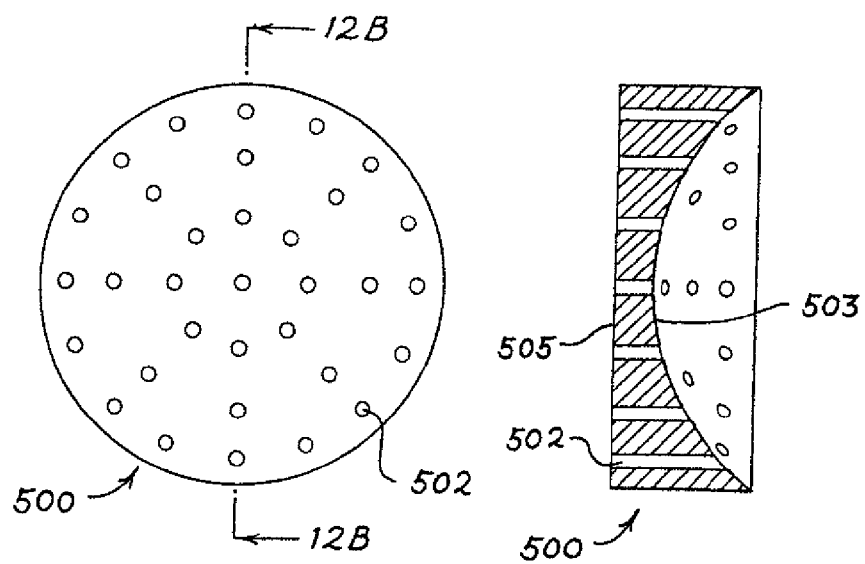
FIGS. 12A and 12B show two views of a piano-concave portion of a contact lens adapted to include a plurality of recording electrodes.
Figure 13:
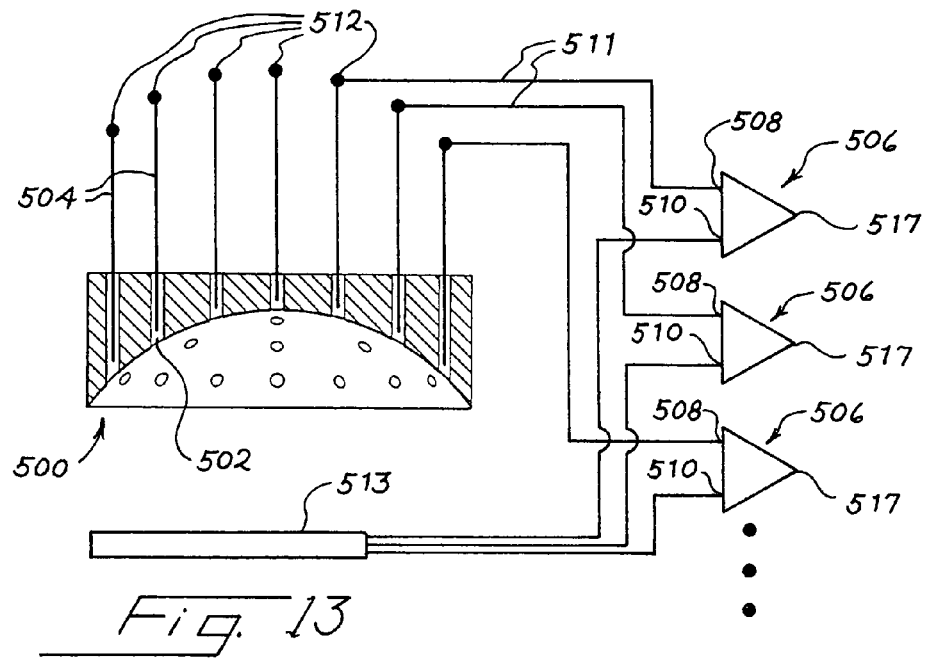
FIG. 13 shows a contact lens electrode array of FIG. 12 in side cross-section, showing connections of the recording electrodes to differential amplifiers.
Figures 14A, 14B:
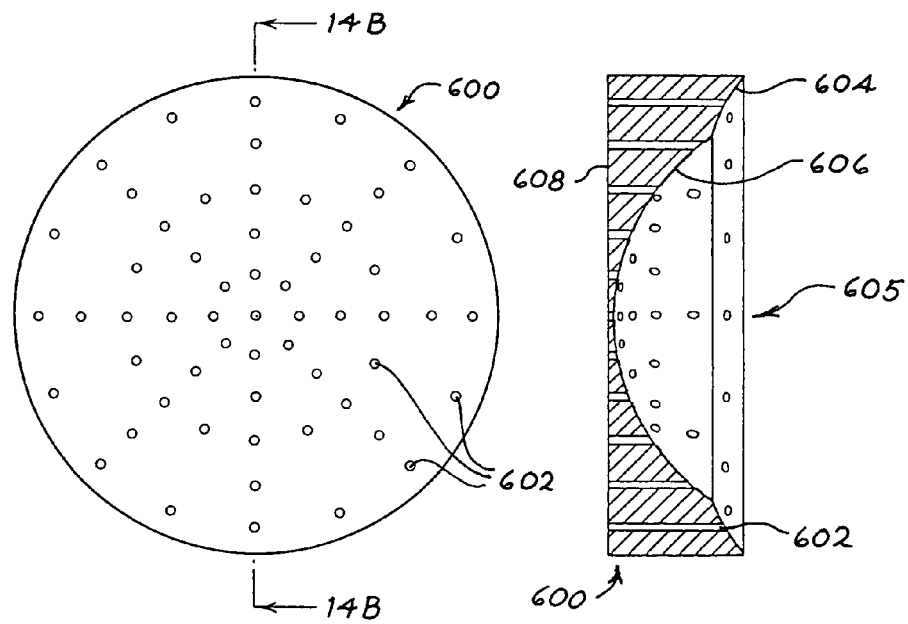
FIGS. 14A and 14B show a detail of a contact lens adapted to accept a plurality of recording electrodes, similar to that shown in FIG. 13.

A third embodiment consists of a contact lens appropriate to fit the subject's cornea (FIGS. 12, 13), or the cornea and anterior sclera (FIG. 14). FIG. 12 shows two views of a portion of a contact lens 500 adapted to include a plurality of recording electrodes. Panel A shows a top plan view and Panel B shows a side cross-section. Through-holes 502 connect the corneal surface 503 of lens 500 with the distal side 505 of the lens 500 at each recording electrode location. In this embodiment, the recording electrode position comprises a through-hole 502, into which a conductive wire, a conductive hydrogel, or a conductive liquid can be placed as the electrode. Through-holes 502 can be lined by a conductive material, which can be in contact with a conductive trace attached to a contact pad.

FIG. 13 shows a contact lens of FIG. 12 in side cross-section, showing connections of the recording electrodes 504 to amplifiers 506 via contacts 512 and wires 511. Each amplifier 506 includes a recording electrode input 508, a reference electrode input 510, and an output 517. The reference electrode inputs 510 of the amplifiers 506 are all connected to a single reference electrode 513, to be placed on the cheek. A conductive rod or wire 504 is positioned in a through-hole 502 in the contact lens 500. The distal end of each active electrode 504 is recessed slightly from the corneal surface of the lens to avoid scratching the cornea. The proximal end 512 of reach electrode 504 functions as the contact point or contact pad in this embodiment. The gap between the distal end of rod 504 and the cornea is occupied by a conductive liquid or hydrogel.

FIG. 14 shows a detail of a contact lens 600 adapted to accept a plurality of recording electrodes, similar to that shown in FIG. 13. Panel A shows a top plan view and Panel B shows a side cross-sectional view. Each recording electrode site 602 is formed as a through-hole connecting the proximal side 605 and distal side 608 of lens 600. In this embodiment, the lens is shaped so that the central portion 606 fits closely to the cornea and a peripheral portion 604 fits closely to the sclera. Recording electrodes 602 are in contact with the cornea and sclera when filled with a conductive liquid or hydrogel, or with a wire, for example. Central portion 606 has a smaller radius of curvature than peripheral portion 604, to accommodate the different radii of curvature of the cornea and sclera, respectively.

The lens substrate may be of neutral or corrective refraction, or may be flat on the surface farthest from the eye surface. At each location where an electrode is desired, a through-hole traverses the lens from the concave corneal surface to the distal or top surface. A wire or other conductive element is introduced into the through-hole to form a complete recording electrode (FIG. 13). When a wire is used, the distal end of the conductive element is slightly recessed from the concave surface of the lens so that the cornea is not directly contacted. The small distance between each conductive element and the corneal surface is occupied by natural or artificial tears or other saline liquid, which is conductive and serves to complete the electrical contact between the corneal surface and the conductive elements.

A fourth embodiment (FIGS. 15, 16) consists of a lens appropriate to fit the subject's cornea, or the cornea and anterior sclera, as described above. Extending beyond the outer edge or periphery of the lens is a ring of lens material with a planar upper surface referred to here as the contact ring. The lens plus contact ring is referred to here as the base lens.

Figure 15A:
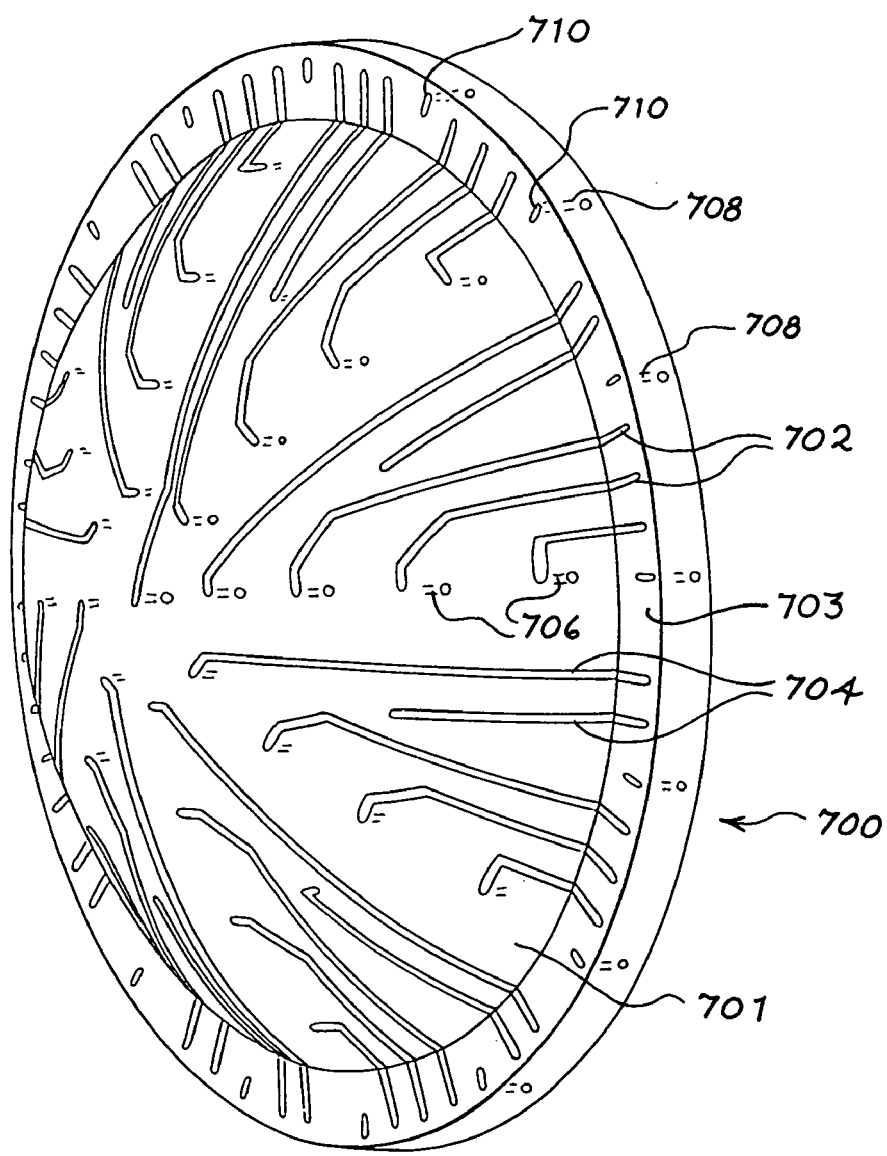
FIGS. 15A and 15B, FIG. 15A shows a partial perspective view of base lens containing a plurality of recording electrodes.
Figure 15B:
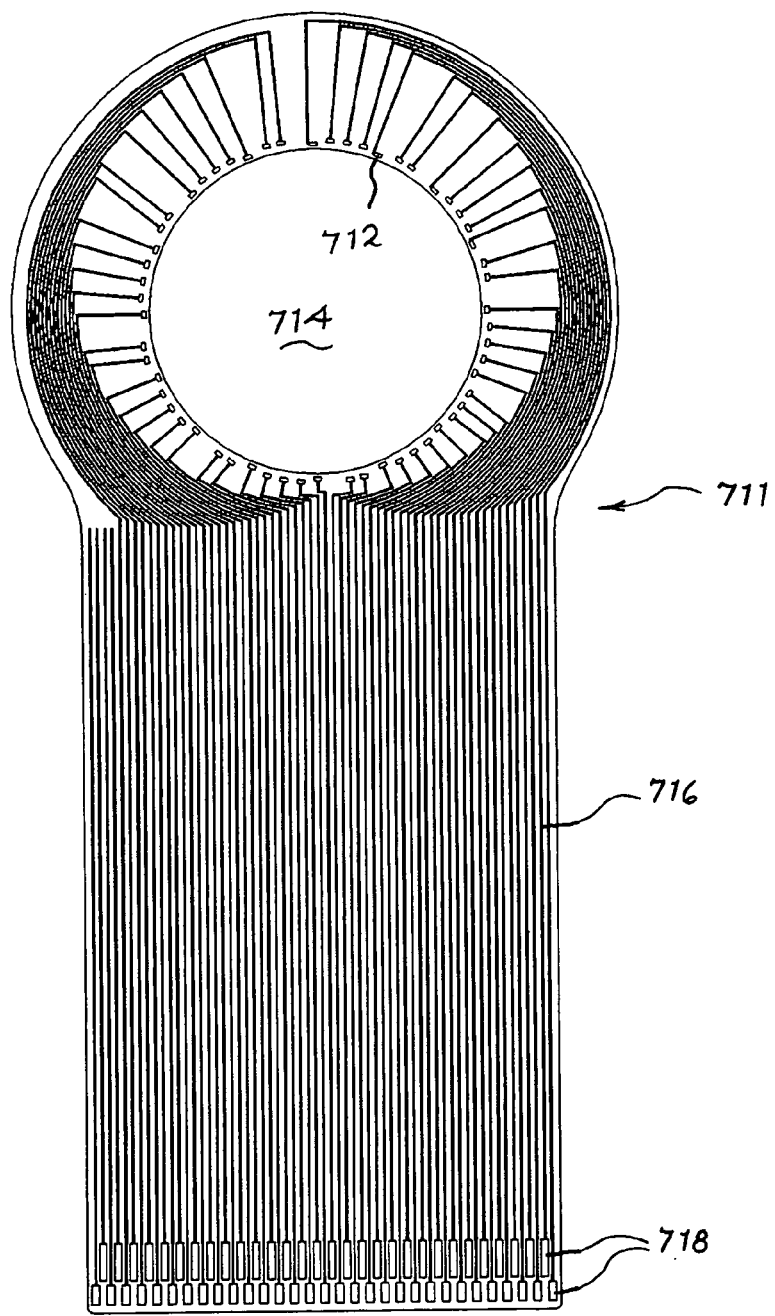

FIG. 15 shows a partial perspective view of base lens 700 containing a plurality of recording electrodes 706 within dome 701 of lens 700 (Panel A), and an interface cable 711 (Panel B). In Panel A, each recording electrode 706 is formed by a through-hole connecting the proximal side of the lens to the distal side, and filled with a conductive liquid or hydrogel. Extending from each recording electrode 706 is a conductive trace 704, which connects electrode 706 to a contact pad 702 (also referred to herein as a "contact") on the peripheral contact ring 703 of the base lens 700. The base lens also includes scleral recording electrodes 708 within the contact ring 703, connected to scleral contact pads 710, also located on contact ring 703. In Panel B interface cable 711 contains a void region 714, which fits around the dome 701 of the base lens 700, such that the contacts 712 on the cable 711 align with the corresponding contact pads 702, 710 on contact ring 703. Extending from each cable contact 712 is a conductive trace 716, which connects the contact 712 to a second contact 718 on the distal end of each conductive trace 716, arranged in such a way as to interface with a signal processor.

Figure 16A:
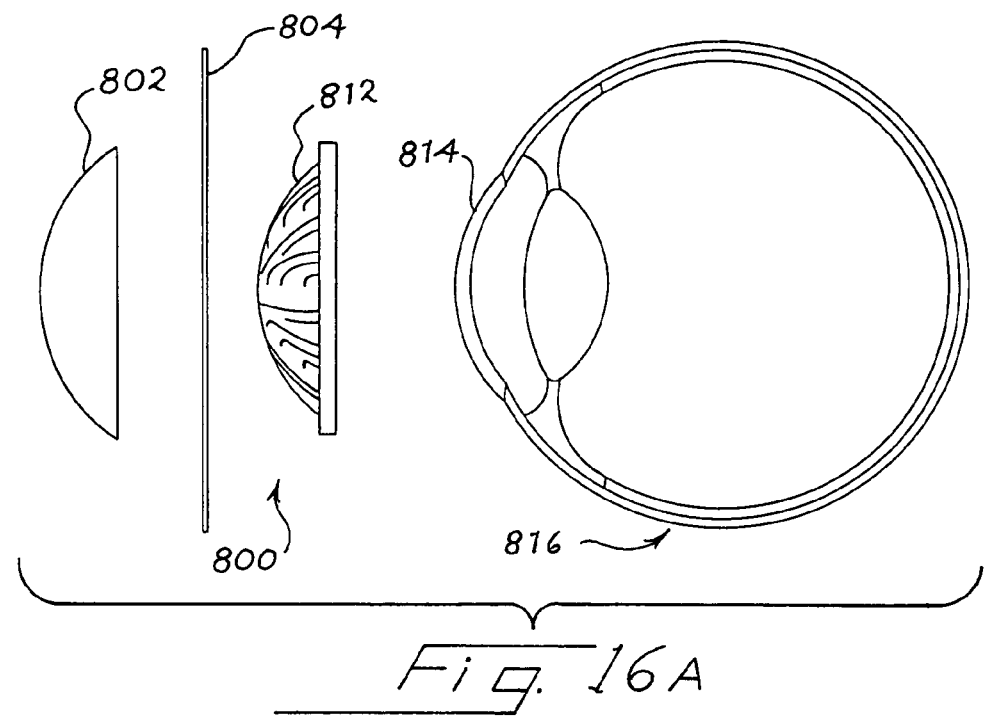
FIGS. 16A and 16B show an assembly of one preferred embodiment of the contact lens containing a plurality of recording electrodes.
Figure 16B:
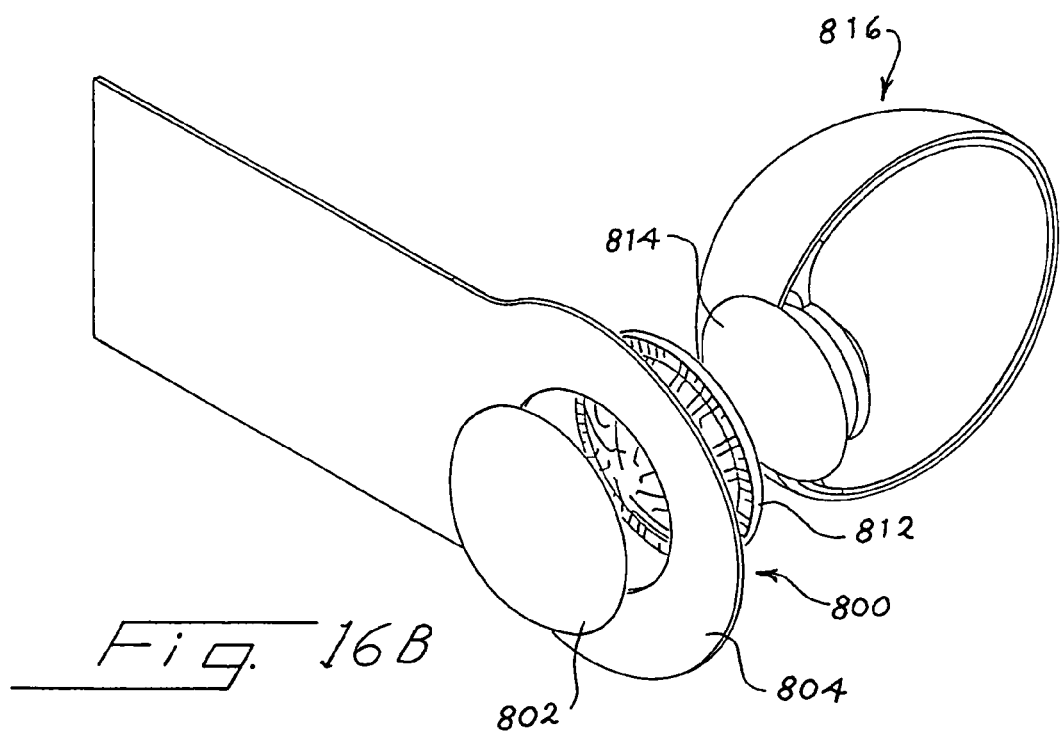

FIG. 16 shows an assembly of one preferred embodiment of the contact lens 800 containing a plurality of recording electrodes, and of substantially similar structure to lens 700 of FIG. 15. Panel A shows an exploded side view of lens 800 and a partial cut-away side view of eye 816, while Panel B shows an exploded perspective view of lens 800 and a partial cut-away perspective view of eye 816. A cap lens 802 is held in contact with the base lens 812, with interface cable 804 in between. The concave surface of the base lens 812 is then brought into contact with the cornea 814 of eye 816.

At each location where an electrode is desired, a through-hole traverses the base lens from the concave corneal surface to the distal or top surface (see e.g., 706, 708 in FIG. 15). A thin layer of conductive material, such as gold, can be deposited on the inner surface of each hole, and in a ring surrounding the opening of each hole on the distal or top surface of the base lens, if desired. A thin layer of gold then forms a conductive trace (see e.g., 704 in FIG. 15) extending from each ring to the planar surface of the contact ring where it terminates in a contact pad. The conductive traces are routed across the top surface of the base lens such that they do not intersect with conductive rings or other traces. A second lens, referred to here as the cap lens 802, is shaped to precisely fit over the base lens 812. Adhering the cap lens 802 to the base lens 812 using an adhesive or solvent serves to electrically insulate the conductive traces from each other. A thin ribbon cable 804 (see e.g., 711 in FIG. 15) is shaped to fit over the contact ring of the base lens, and contains electrical contacts (see e.g., 712 in FIG. 15) that align with the contact pads (702, 710) on the contact ring. This ribbon cable 804 is held in place by being sandwiched between the cap lens 802 and base lens 812. The ribbon cable 804 serves to connect each contact to the input of a signal processor. Electrical contact is obtained between the gold lining the holes and the cornea through natural or artificial tears or other conductive liquid or hydrogel, which fills each hole. Thus, each location on the eye surface that is positioned under a hole is electrically connected to the input of a signal processor.

A Computational Method.

None of the models described in the prior art have any of the following properties, all of which are provided by the present invention:

(a) Explicit specification of the geometry and electrical properties of the following ocular and peri-ocular structures: tear film, retinal nerve fiber layer, outer limiting membrane, photoreceptor layer, retinal pigment epithelium, adipose tissue, intraocular muscles, choroid.

(b) Spatial distribution of individual cell types, such as rod photoreceptors, cone photoreceptors, bipolar cells, horizontal cells, Muller cells, amacrine cells, or ganglion cells. These differences are manifest in the model as spatial differences in the charges, potentials or currents that represent the bioelectric activity of the retina.

(c) Spatial differences in retinal thickness, such as the macular region, fovea, optic nerve head, or known regions of retinal thinning due to disease or trauma as indicated by ophthalmic exam.

Another aspect of the present invention is a computational method for using simultaneously recorded potentials from multiple locations on the eye surface to estimate the magnitude and location of retinal activity. The method includes an algorithm which makes use of the recorded eye surface potentials and a computational model of the eye. The result of executing the algorithm is a set of values that describes the magnitude of retinal activity at a number of specific locations across the retina. The magnitudes may also be attributed to specific cell types or neural pathways in the retina.

The measured eye surface potentials are recorded subsequent to the delivery of a stimulus to the eye. The stimulus can be any of the variations used in clinical or research electroretinography, including full-field stimuli that vary in spectral content or luminance or temporal kinetics. The stimulus may be delivered to an eye that is preconditioned with a baseline condition of light exposure, such as full dark adaptation, or adaptation to a constant luminance of specific value, or a preconditioning light flash, as might be used to probe the process of retinal recovery from such a flash. The specific characteristics of the stimulus are chosen in order to probe the response of a particular cell type or neural pathway in the retina. For example, full field brief flash stimulus of low luminance presented to a dark adapted eye will preferentially probe the rod pathway. Variations of full-field stimuli presented include brief flashes, step increases or decreases in luminance, saw-tooth variations in luminance, long series of brief flashes, or a paired-flash protocol. Stimuli may also be presented which are not uniform across the visual field, comprised of specific areas within the visual field which vary in luminance or spectral content.

The measured eye surface potentials preferably are values derived from the voltage versus time waveforms recorded by the plurality of recording electrodes in contact with the eye. The recorded waveforms are processed by application of digital filters for the purpose of reducing the noise in the recorded signals. Preferably, the recorded waveforms are further processed by calculating a difference between the waveform recorded by each electrode and the waveform recorded by a reference electrode or any combination of the remaining recording electrodes. The resulting difference waveforms may be further processed by the application of filters to isolate specific components of the recorded response. For example, to isolate the electroretinogram oscillatory potentials, the difference waveforms may be processed by the application of a band-pass filter of passband 100-150 Hertz. If desired, the signal to noise ratio can be increased by averaging together waveforms recorded from the same electrode following separate, but similar, stimuli.

Following the processing steps just described, the waveforms associated with each electrode location are analyzed for amplitude or other feature at a specific time, where the time chosen corresponds to a known physiological event in the retina. For example, if the stimulus was a brief flash of low luminance presented to a dark adapted eye, the initial negative excursion of the resulting waveform is associated with the activity of the retinal rod photoreceptor cells. Analysis of the waveform at the time of the first negative peak, or at a fixed time preceding this peak, will be a measure of rod photoreceptor activity.

Following analysis of waveforms for amplitude, a set of eye surface potential values results, with one value for each electrode location. Let these values be designated $C_i$, where i is the index of a specific electrode.

Figure 17:
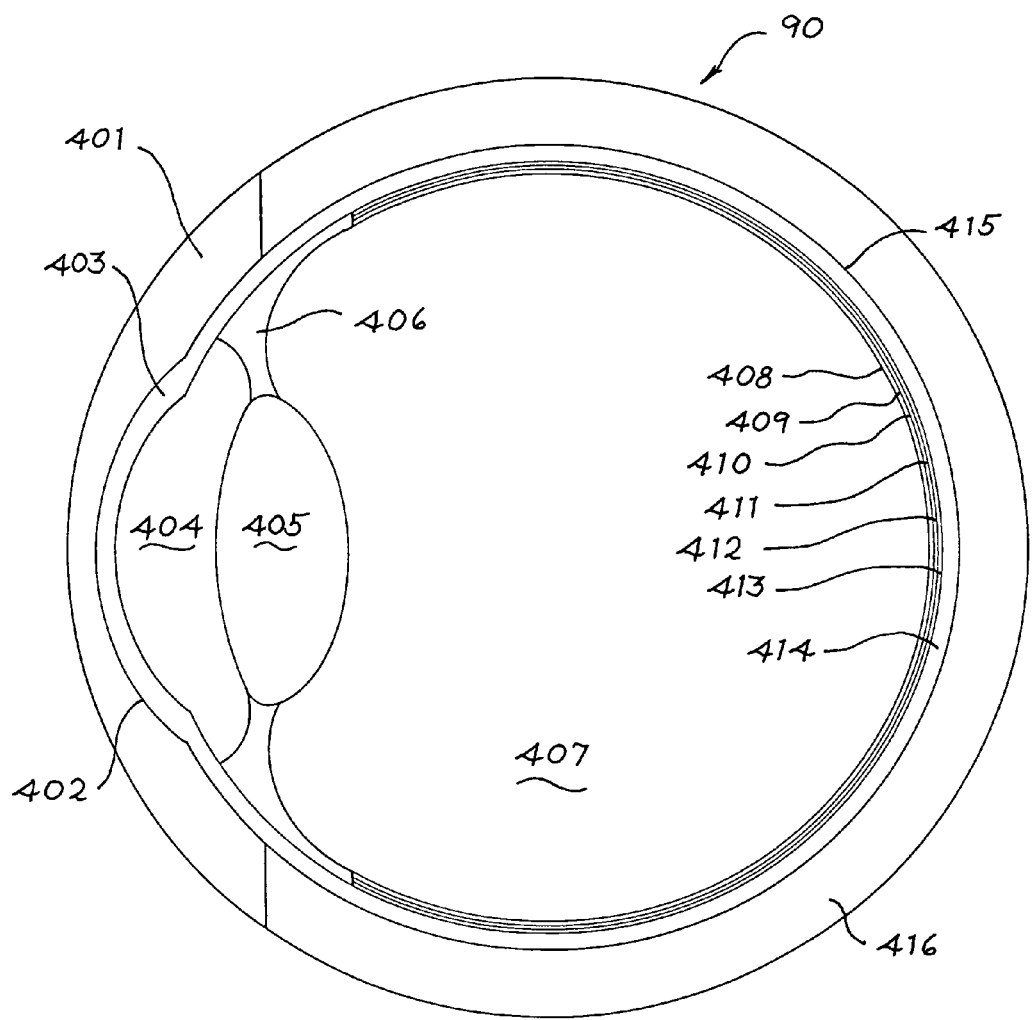
FIG. 17 shows a schematic representation of a model of the human eye.

In the algorithm, the set of values $C_i$ is used in conjunction with a three-dimensional computational model of the eye, which embodies the anatomy and electrical properties of the eye and surrounding tissue. For a typical human eye, a two-dimensional representation of the model structure is illustrated in FIG. 17, which shows a model of a human eye generally indicated at 90. Included in the model is an air space 401 and an anterior tear film 402 located in front of a cornea 403. An anterior chamber 404, a lens 405 and vitreous humor 407 lie behind the cornea, as shown. A cilliary body and zonule fiber 406 are located at either side of lens 405. As indicated at the right hand end of FIG. 17, the interior of the eye includes a retinal nerve fiber layer 408. Reference number 409 refers to the neural retina, including the ganglion cells, amacrine cells, horizontal cells, bipolar cells, and Muller cells. An outer limiting membrane 410 lies in front of the array of rods and cones indicated at 411. Numeral 412 refers to the retinal pigments epithelium/R-membrane. Also included is a choroid 413 and a sclera 414. Posterior tear film is indicated at 415 and adipose/muscle tissue is indicated at 416.

As an example of one implementation of the model, the anatomical components of the model are listed in Table 1. For eyes of other species, the structure and electrical properties are altered appropriately. Appropriate electrical properties are assigned to each component of the model. The electrical property assigned may be conductivity, resistivity, permittivity, or permeability. The structure and electrical properties of the model are converted to a set of nodes, such that a numerical method may be applied to solve for the potentials, charges or currents at each node. Appropriate numerical methods include the boundary element method, finite element method, finite volume method, and finite difference method. The spacing of the nodes is chosen such that the difference in potential or current between adjacent nodes is acceptably small.

TABLE 1

| Model element | Thickness (mm) | Conductivity (S/m³) |
| --- | --- | --- |
| Air | 0.4375 | 0 |
| Anterior Tear Film | 0.02 | 1.5 |
| Cornea | 0.2539 | 0.422 |
| Anterior Chamber | 0.6427 | 1.5 |
| Lens | 3.6883 | 0.3222 |
| Vitreous Humor | 1.2552 | 1.5 |
| Retinal Nerve Fiber Layer | 0.090 | 0.5028 |
| Ganglion Cells, Amacrine Cells, Horizontal Cells, Bipolar Cells, Muller Cells | 0.108 | 0.5028 |
| Outer Limiting Membrane | 0.020 | 0.109 |
| Rod and Cone Photoreceptor Cells | 0.040 | 0.5028 |
| Retinal Pigment Ephithelium | 0.010 | 0.109 |
| Choroid | 0.040 | 0.2779 |
| Sclera | 0.147 | 0.5028 |
| Posterior Tear Film | 0.02 | 1.5 |
| Adipose Tissue | 0.4253 | 0.02081 |

The retinal area in the model may be subdivided into a number of sub-areas equivalent to or exceeding the number of electrodes, referred to herein as "source areas". The source areas may be of equal area, or be scaled according to a feature of the retina, such as the spatial density of specific types of retinal cells (see FIG. 18).

The retinal activity within each source area is simulated by a potential difference, charge separation or current source assigned to each source area. Each source area may also be approximated as an equivalent dipole voltage or current, which has a location centered within the source area. This approach will be considered for the following description.

The dipole is implemented as a charge separation, potential, or non-conserved current source, across the entire thickness of the retina, or across a specific sublamina of the retina as appropriate for the anatomical position of the retinal cell type which gives rise to the electroretinogram response component of interest. For example, if the rod photoreceptor response is being analyzed, the dipole charge separation will be implemented across the photoreceptor layer, namely from the boundary between the photoreceptor outer segments and the retinal pigment epithelium to the outer plexiform layer. The direction of the dipole is determined by the axial direction of the retinal cell orientation at that location, which is generally along a radial line extending from the anatomical center of the eye. However, for photoreceptors, the direction is radial from the optical principle point of the eye, located within the lens.

The unknown parameter of each equivalent dipole is magnitude. The main purpose of the algorithm is to solve for these magnitudes. These magnitudes represent the magnitude of retinal activity at the source area occupied by the equivalent dipole. Let the set of these retinal magnitudes be designated as $R_j$, where j is the index of the specific source area of the retina. For 50 electrodes, there will be 50 waveforms recorded, and 50 potential values, $C_i$, i=1-50, extracted from these waveforms. The values $R_j$ are related to the values $C_i$ through a transfer matrix. The quantities in the transfer matrix are obtained by solving the forward problem.

To solve the forward problem, one equivalent dipole $R_j$ is assigned a starting value, the remaining dipoles are assigned a value of zero, and the resulting values $C_i$ are calculated using the model and an appropriate numerical solving method, such as the finite element method. Each dipole, j, is iteratively assigned the starting value in turn, until all dipoles have been used to solve for eye surface potential values. For each dipole $R_j$, a weighting term, $W_{i,j}$, is thus determined which relates the location of that dipole with the eye surface potential at each electrode location. For 50 source areas, the result is a set of 50 weight values for each electrode location, where each of these 50 weight values represents the contribution of one retinal source area to the potential recorded by that electrode. For 50 electrodes, the entire transfer matrix is then 50×50 entries. For illustration, a transfer matrix for 4 electrodes, and four retinal source areas, is given in Table 2.

TABLE 2

| Eye surface electrode positions | Retinal source areas. | | | |
|---|---|---|---|---|
| | $R_1$ | $R_2$ | $R_3$ | $R_4$ |
| $C_1$ | $W_{1,1}$ | $W_{1,2}$ | $W_{1,3}$ | $W_{1,4}$ |
| $C_2$ | $W_{2,1}$ | $W_{2,2}$ | $W_{2,3}$ | $W_{2,4}$ |
| $C_3$ | $W_{3,1}$ | $W_{3,2}$ | $W_{3,3}$ | $W_{3,4}$ |
| $C_4$ | $W_{4,1}$ | $W_{4,2}$ | $W_{4,3}$ | $W_{4,4}$ |

With the set of weights $W_{i,j}$ thus determined, a set of starting values $R_j$ is assumed, and a set of estimated corneal potentials, $C'_i$, is calculated by assuming linear superposition. For the example of 4 electrodes illustrated in the table above:

$$C'_1 = [(R_1 W_{1,1}) + (R_2 W_{1,2}) + (R_3 W_{1,3}) + (R_4 W_{1,4})] S_1$$

where $S_i$ is a scaling factor. Each $W_{i,j}$ represents the contribution of $R_j$ to $C_i$.

In practice the corneal potentials $C_i$ are recorded, and are compared to the estimated values $C'_i$ by calculating an error term, such as a summed squared error term, $E = \Sigma (C_i - C'_i)^2$. A nonlinear minimization approach is then applied to minimize E by iteratively changing the values of $R_j$. The set of values $R_j$ that results in a minimum value of E is taken to reflect the magnitudes of retinal activity within each source area of retina represented by each value of $R_j$.

In one preferred embodiment of the algorithm for estimating retinal activity from the simultaneously recorded electroretinogram potentials, a three-dimensional computational model of a human eye is constructed in the finite element software package ANSYS. The model has the anatomical and electrical properties listed in Table 1. If a contact lens electrode array containing 33 electrodes is utilized to record the eye surface potentials, the retina portion of the model is divided into 33 sub-areas (retinal source areas) of approximately equal area. Each source area is assigned an equivalent dipole source, which is modeled as a separation of charge across the retina, with positive charge on the proximal, or vitreal, surface and negative charge on the distal surface. The charges are assigned to the finite element node nearest the center of each retinal source area on each surface of the retina, resulting in a dipole direction that is approximately along a line radiating from the anatomical center of the eye. For each source area, the equivalent dipole is assigned a default magnitude in Coulombs. The forward problem, which predicts the distribution of eye surface potentials for a given distribution of retinal activity, is then solved once for each equivalent dipole when all other dipoles are assigned a magnitude of zero.

For each dipole simulation, the potential at each electrode location on the eye surface is recorded as a weight, relating the contribution of that dipole to each electrode. When all dipoles have been simulated, there exist a set of weights related all dipoles to each electrode location. These weights are then entered into a transfer matrix in MATLAB® or other suitable computer program capable of performing linear algebraic operations. The eye surface potential at a given electrode location is predicted to be the linear sum of contributions from all retinal source area equivalent dipoles, where each contribution is the product of the weight and the magnitude of activity for that retinal source area. An error measure is calculated, which preferably is equal to the square root of the sum of the squared differences between the measured and calculated potential values across all electrode locations. A standard non-linear minimization algorithm, also called a non-linear regression algorithm, such as that performed by the MATLAB® function "FMINSEARCH" is then used to minimize the error measure by searching for optimal values of magnitude for each equivalent dipole. The final set of magnitudes is then interpreted as the distribution of physiological activity across all retinal source areas. The distribution of physiological activity is thus a map of retinal function, which can be displayed in a convenient graphical format, such as a surface plot, bubble plot, or color plot.

Figure 18B:
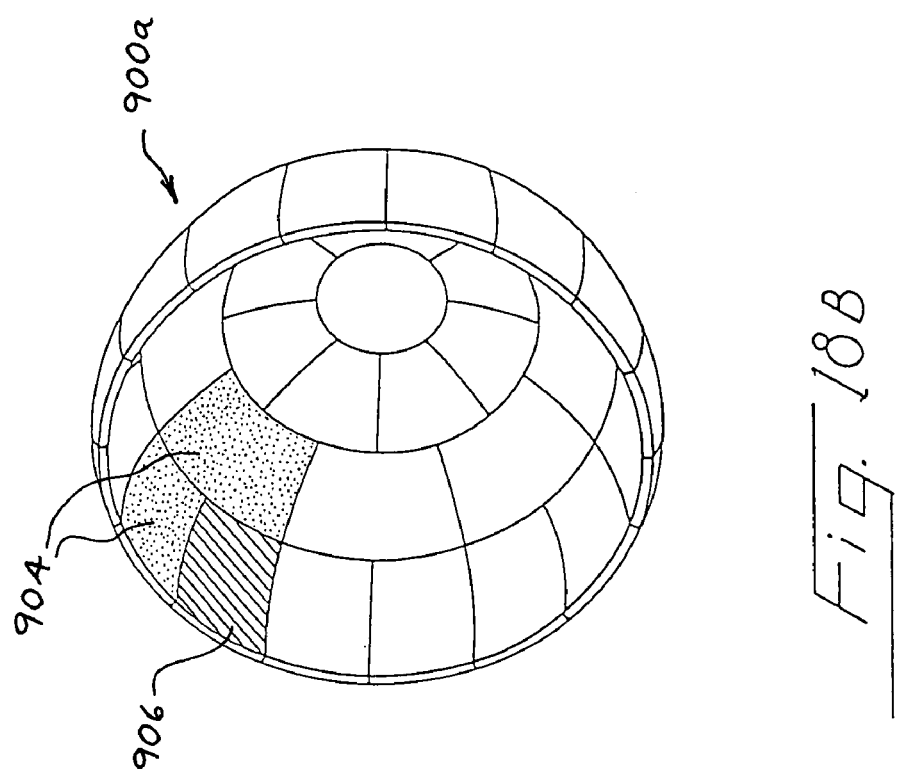
FIGS. 18A and 18B show a representation of a retina from a model of the eye.
Figure 18A:
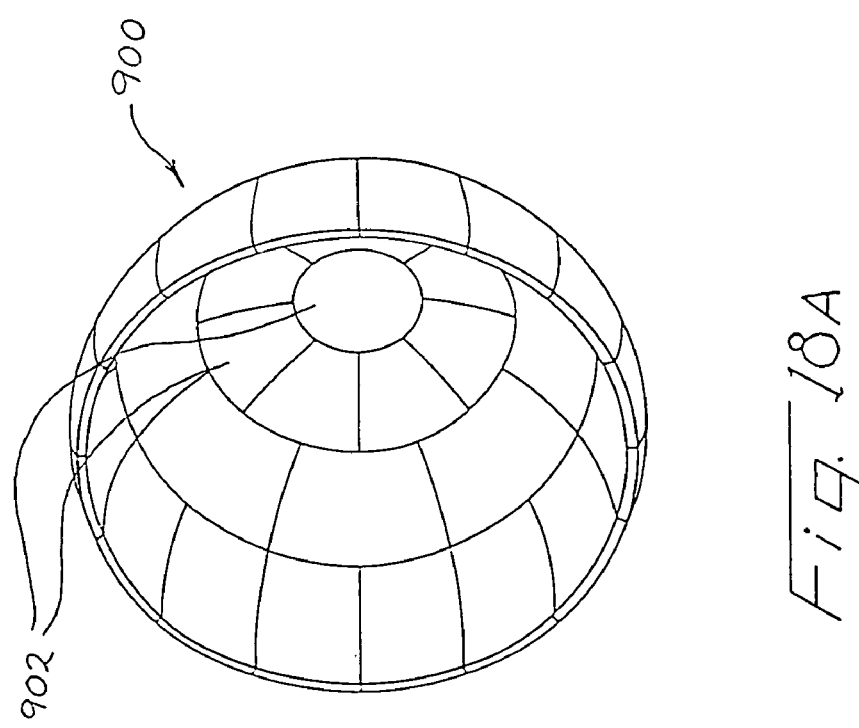

FIG. 18, in Panel A, shows a schematic representation of a retina 900 from a model as described herein divided into 33 source areas 902. Panel B shows a representation of a retinal map obtained by the methods of the invention, in which sources areas are stippled or striped to indicate a lower level of retinal activity relative to the other source areas. In Panel B, source areas with no stippling or stripes represent source areas with relatively uniform, normal retinal activity. Areas with stippling (indicated by numerals 904) represent areas of moderate retinal impairment, while the striped area 906 represents a portion of the retina with a severe impairment of retinal function.

The foregoing description and the accompanying drawings are illustrative of the present invention. Additional variations and arrangements of parts are possible without departing from the spirit and scope of this invention.

What is claimed is:

1. An electrode array device for simultaneously detecting electrical potentials at five or more locations on the anterior surface of an eye, the device comprising:
   a transparent or translucent dielectric lens substrate having a concave inner surface conforming to the cornea on the exterior surface of the eye;
   at least 5 recording electrodes positioned in relation to the inner surface of the lens substrate so as to make electrical connection with the cornea when the lens substrate is placed over the cornea on the exterior surface of the eye;
   wherein each recording electrode is in electrically conductive communication with a corresponding conductive contact, there being one conductive contact for each electrode, each conductive contact being adapted for operable connection to a signal processor, and each conductive contact being electrically insulated from the anterior surface of the eye.

2. The device of claim 1 wherein the lens substrate includes 5 to 500 recording electrodes.

3. The device of claim 1 wherein each recording electrode comprises a conductive material deposited on the concave surface of the lens substrate.

4. The device of claim 1 wherein each conductive contact is positioned in the peripheral region of the lens substrate, and is connected to its corresponding recording electrode via an electrically conductive trace that is electrically insulated from the surface of the eye.

5. The device of claim 4 wherein each recording electrode comprises a cylindrical through-hole formed in the lens substrate adjacent to an un-insulated portion of its corresponding conductive trace, such that an electrically conductive connection is made between the conductive trace and the anterior surface of the eye when the lens substrate is placed on the anterior surface of the eye in the presence of an amount of an electrically conductive liquid or hydrogel sufficient to fill each through-hole and connect with the un-insulated portion of the trace.

6. The device of claim 5 wherein each through-hole is lined with a conductive material in electrically conductive connection with the conductive trace.

7. The device of claim 6 wherein the conductive material lining each through-hole comprises a metal, conductive polymer, or semiconductor material.

8. The device of claim 4 wherein each conductive trace, active electrode, and contact pad comprises a metal, conductive polymer, or semiconductor material.

9. The device of claim 1 wherein the lens substrate is configured to provide corrective refractive power to correct for defects in the visual acuity of the eye.

10. The device of claim 1 wherein the lens substrate is plano-concave.

11. The device of claim 1 wherein each recording electrode comprises a conductive element passing through the lens substrate.

12. The device of claim 1 further comprising one or more scleral recording electrodes positioned to make electrical contact with the sclera of the eye when the lens substrate is placed on the anterior surface of the eye, each scleral electrode being in electrically conductive communication with a corresponding conductive scleral electrode contact, there being one scleral electrode contact for each scleral electrode, each scleral electrode contact being adapted for operable connection to a signal processor, and each scleral electrode contact being electrically insulated from the anterior surface of the eye.

13. The device of claim 12 wherein each scleral recording electrode contact is positioned in a peripheral region of the lens substrate, and is connected to its corresponding scleral electrode either directly or via an electrically conductive trace that is electrically insulated from the anterior surface of the eye.

14. The device of claim 13 wherein each scleral recording electrode comprises a cylindrical through-hole formed in the lens substrate adjacent to its contact or to an un-insulated portion of its corresponding conductive trace, such that an electrically conductive connection is made between the contact and the anterior surface of the eye when the lens substrate is placed on the anterior surface of the eye in the presence of an amount of electrically conductive liquid or hydrogel sufficient to fill each through-hole and connect with the contact or un-insulated portion of the trace.

15. An electroretinographic (ERG) system comprising an electrode array device of claim 1 in which each recording electrode thereof is in electrically conductive communication with a signal processor including an amplifier, and capable of amplifying and detecting electrical potential signals from each electrode in a form suitable for data analysis.

16. The ERG system of claim 15 wherein the signal processor is incorporated in a computer.

17. The ERG system of claim 16 further comprising a computer programmed to generate a map of retinal activity from the electric potential signals.

18. The device of claim 1 wherein each of the recording electrodes comprises a separate through-hole defined by the lens substrate in the portion of the substrate conforming to the cornea, each through-hole containing a conductive fluid or gel, and a conductive element adapted to contact the conductive fluid or gel present within the through-hole and thereby provide a conductive contact with the cornea during use.

19. The ERG system of claim 17 wherein the electric potential signals are detected by the recording electrodes after stimulation of the retina with a light source, and the signals are analyzed according to the position of the electrode from which each signal was obtained to produce a map of the retina indicating spatial differences in the contribution of the retina to the recorded signals.

* * * * *